United States Patent
Alani

(10) Patent No.: US 10,016,422 B2
(45) Date of Patent: Jul. 10, 2018

(54) NANOCARRIER DRUG DELIVERY PLATFORM

(71) Applicant: Oregon State University, Corvallis, OR (US)

(72) Inventor: Adam W. G. Alani, Beaverton, OR (US)

(73) Assignee: Oregon State University, Corvallis, OR (US)

( * ) Notice: Subject to any disclaimer, the term of this patent is extended or adjusted under 35 U.S.C. 154(b) by 0 days.

(21) Appl. No.: 15/281,822

(22) Filed: Sep. 30, 2016

(65) Prior Publication Data

US 2017/0087095 A1 Mar. 30, 2017

Related U.S. Application Data

(60) Provisional application No. 62/235,195, filed on Sep. 30, 2015.

(51) Int. Cl.

| | |
|---|---|
| A61K 9/51 | (2006.01) |
| A61K 31/506 | (2006.01) |
| A61K 31/337 | (2006.01) |
| A61K 31/436 | (2006.01) |
| A61K 31/5377 | (2006.01) |
| A61K 31/519 | (2006.01) |

(Continued)

(52) U.S. Cl.
CPC .......... *A61K 31/506* (2013.01); *A61K 9/0019* (2013.01); *A61K 9/5146* (2013.01); *A61K 31/337* (2013.01); *A61K 31/436* (2013.01); *A61K 31/519* (2013.01); *A61K 31/5377* (2013.01); *B82Y 5/00* (2013.01)

(58) Field of Classification Search
None
See application file for complete search history.

(56) References Cited

U.S. PATENT DOCUMENTS

| 5,582,172 A | 12/1996 | Papisov et al. |
| 2009/0191152 A1 | 7/2009 | Forrest et al. |

(Continued)

FOREIGN PATENT DOCUMENTS

| WO | WO 2002/102354 | 12/2002 |
| WO | WO 2014/165728 | 10/2014 |

OTHER PUBLICATIONS

Letchford et al., Eur. J. Pharm. Biopharm., 2007, vol. 65, pp. 259-269.*

(Continued)

*Primary Examiner* — Brian M Gulledge
(74) *Attorney, Agent, or Firm* — Klarquist Sparkman, LLP

(57) ABSTRACT

Disclosed herein are embodiments of a composition comprising a drug in a polymer nanoparticle. The nanoparticles may have a size and/or a surface potential selected to facilitate lymph node uptake and/or dissemination throughout the lymphatic system. The nanoparticle may be a polyethyleneglycol-block-poly(ε-caprolactone) (PEG-PCL) nanoparticle. Also disclosed are embodiments of a method of using the composition. The composition may be administered subcutaneously. The drug-loaded nanoparticles are useful for treating certain cancers and/or decreasing the number of melanocytes in lymph nodes that are proximal to, distal to or both proximal and distal to a site of administration.

17 Claims, 22 Drawing Sheets

(51) Int. Cl.
*A61K 9/00* (2006.01)
*B82Y 5/00* (2011.01)

(56) References Cited

U.S. PATENT DOCUMENTS

| | | |
|---|---|---|
| 2009/0312402 A1 | 12/2009 | Contag et al. |
| 2013/0336889 A1 | 12/2013 | Shieh et al. |
| 2014/0079774 A1* | 3/2014 | Brinker .................. C07K 14/47 424/450 |
| 2015/0023909 A1 | 1/2015 | Abraham et al. |

OTHER PUBLICATIONS

Rao et al., J. Pharm. Sci., 2010, 99(4), pp. 2018-2031.*
Flaherty et al., "Combined BRAF and MEK Inhibitors in Melanoma with BRAF V600 Mutations," *The New England Journal of Medicine 367*(18):1694-1703, Nov. 1, 2012.
Khan et al., "Advanced Drug delivery to the lymphatic system: lipid-based nanoformulations," *International Journal of Nanomedicine* 8:2733-2744, Jul. 25, 2013.
Rao et al., "Biodegradable PLGA Based Nanoparticles for Sustained Regional Lymphatic Drug Delivery," *Journal of Pharmaceutical Sciences* 99(4):2018-2031, published online Nov. 9, 2009.

* cited by examiner

NANOCARRIER DRUG DELIVERY PLATFORM

CROSS REFERENCE TO RELATED APPLICATION

This claims the benefit of U.S. provisional patent application No. 62/235,195, filed Sep. 30, 2015, which is incorporated herein by reference in its entirety.

FIELD

This disclosure concerns a composition comprising at least one drug and a nanoparticle, and a method of using the composition to treat cancer.

BACKGROUND

Melanoma is the deadliest form of skin cancer with a very high mortality rate. Metastatic melanoma has a high mortality rate due to lymphatic progression of the disease. The standard treatment for early stage diagnosis is surgical removal of the tumor and for late stage surgery followed by radiation and chemotherapy. Tumor metastasis is the major reason for high mortality rates in melanoma. The process begins with the detachment of tumor cells from the adjacent endothelial cells and the basement membrane and is accompanied by the secretion of various cytokines and growth factors. Migration through the lymphatic vasculature is preferred over blood vessels because of reduced flow rates and pressure, easier access to the vessel, and wider vessel lumens. Up to 80% of melanomas metastasize occurs through the lymphatic system. Additionally, tumor cells secrete lymphangiogenic growth factors like Vascular Endothelial Growth Factors that can stimulate lymphangiogenesis and further promote lymphatic migration. These enlarged lymphatic vessels act as a freeway for the metastatic cells to gain access and spread to distal lymph nodes (LN) and organs.

Extensive research over the past two decades has helped us elucidate the driver mutations occurring in different oncogenes involved in the development of metastatic melanoma. The majority of the studied mutations occur primarily in the BRAF (a serine/threonine protein kinase) genes and the FDA have approved targeted therapies for patients in stage IV or unresectable melanoma. However, newer emerging genetic targets include Neuroblastoma—Rat Sarcoma (NRAS) and nuclear receptors like Retinoid X Receptor-α (RXRα) genes. In pathological conditions, point mutations at the codon 61 of NRAS (NRAS$Q^{61K}$) gene locks the activated form of NRAS-GTP thereby promoting continuous up regulation of downstream effector proteins and signaling pathways in the malignant melanoma phenotype. Activated NRAS$^{Q61K}$ mutations play a significant role in the development of metastatic melanoma and are the primary driver mutations that are responsible for the spread of the disease in humans. These oncogenic drivers promote angiogenesis and invasiveness of the malignant cells and also help to develop larger nevi when compared to the BRAF mutations. RXRα plays a major role in gene expression and signal transduction, and in human melanomas the expression of RXRα is lost as the disease progresses. Animal studies have indicated that the loss of RXRα can lead to the increased melanocyte proliferation and the formation of malignant melanomas. Thus, while therapies targeting the BRAF mutations exist, no such therapeutic approaches are currently available for the NRAS or RXRα mutations.

SUMMARY

Disclosed herein are embodiments of a composition comprising a drug and a nanoparticle encapsulating the drug. The nanoparticle may have a size and zeta potential effective to cause uptake of the composition into at least one lymph node of a subject to which the composition is administered. In some embodiments, the size and zeta potential are selected to facilitate uptake into at least one lymph node, and may be to facilitate uptake to at least one lymph node distal to a site of administration. The size and zeta potential may also be selected to facilitate dissemination to lymph nodes throughout the lymphatic system, such as to lymph nodes both proximal and distal to a site of administration. The nanoparticle may be a polyethyleneglycol-block-poly (ε-caprolactone) (PEG-PCL) nanoparticle. In some embodiments, the drug is docetaxel, everolimus, LY294002, paclitaxel, rapamycin, irinotecan, ixabepilone, vinblastine, vinorelbine, estramustine, vemurafenib, trametinib, dabrafenib or a combination thereof, and in certain embodiments, the drug is docetaxel, everolimus and LY294002, and in other certain embodiments, the drug is trametinib and dabrafenib.

The nanoparticle may have a zeta potential of from −1 mV to −39 mV, such as from −10 mV to −20 mV. The nanoparticle may have a size of from 20 to 80 nm, such as from 20 nm to 50 nm. In some embodiments, each drug has a drug concentration in the composition of from 0.5 mg of drug per mL of nanoparticle solution to 2 mg of drug per mL of nanoparticle solution, and the drug concentration may be stable for 24 hours after formulation, and may be within 6% of the original drug concentration. In certain embodiments, the composition has a partially charged surface and a size of 50 nm. In certain embodiments, the nanoparticle has a size of from 40 nm to 50 nm and a zeta potential of from −15 mV to −20 mV.

Pharmaceutical compositions are also contemplated, comprising a disclosed nanoparticle/drug composition and a pharmaceutically acceptable carrier or excipient. The pharmaceutical composition may be formulated for subcutaneous administration and/or intramuscular administration.

Also disclosed are embodiments of a method of treating cancer in a subject, such as a human or other mammalian subject. The method may comprise administering to the subject a therapeutically effective amount of a disclosed composition or pharmaceutical composition. The cancer may be a metastatic cancer, and in some embodiments, the cancer is a melanoma. The cancer may be a solid tumor cancer. In some embodiments, the cancer is cutaneous melanoma, inflammatory breast carcinoma, non-small cell lung cancer, muscle-invasive transitional cell carcinoma of the bladder, and head and neck cancer, or a combination thereof. Administration may be subcutaneous administration and/or intramuscular administration. In some embodiments, administering to the subject comprises administering an amount of the composition sufficient to decrease the number of melanocytes in at least one lymph node of the subject. The composition may be administered at a site proximal to the lymph node and/or distal to the lymph node. The amount of the composition administered may be sufficient to decrease the number of melanocytes in lymph nodes both proximal and distal to the site of administration and/or throughout the lymphatic system. In some embodiments, administering to the subject comprises administering an amount of the composition sufficient to be taken up by a lymphatic system and disseminated to at least one lymph node distal to a site of administration, and may be sufficient to be disseminated to lymph nodes throughout the lymphatic system.

The foregoing and other features and advantages of the invention will become more apparent from the following detailed description, which proceeds with reference to the accompanying figures.

BRIEF DESCRIPTION OF THE DRAWINGS

FIG. 4 is a graph of concentration versus time illustrating the initial loading and drug retention at 24 hours for DTX, EVR, and LY in three-drug neutral, partially charged, and fully charged nanoparticles (Mean±S.D, n=3), with the numbers indicating average loading concentrations for each individual drug in the nanoparticles.

DETAILED DESCRIPTION

Figure 1A:
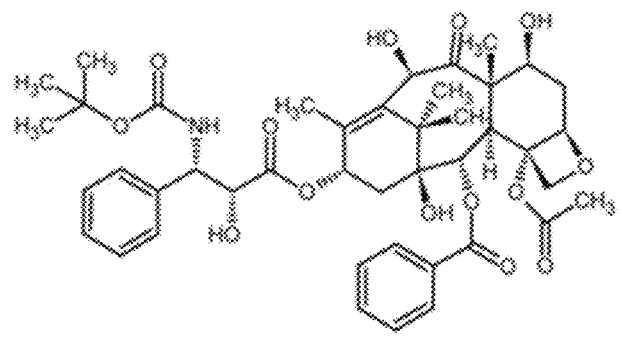
FIG. 1A shows the structure of docetaxel (DTX).

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

The terms "administer," "administering," "administration," and the like, as used herein, refer to methods that may be used to enable delivery of compositions to the desired site of biological action. These methods include, but are not limited to, intraarticular (in the joints), intramuscular, intratumoral, intradermal, intraperitoneal, subcutaneous (SC), orally, topically, intrathecally, inhalationally, transdermally, rectally, and the like. Administration techniques that can be employed with the agents and methods described herein are found in e.g., Goodman and Gilman, The Pharmacological Basis of Therapeutics, current ed.; Pergamon; and Remington's, Pharmaceutical *Sciences* (current edition), Mack Publishing Co., Easton, Pa. In particular embodiments, administration refers to subcutaneous administration. In other embodiments, administration refers to intramuscular administration. In some embodiments, the term administration does not include intravenous administration.

The term "effective amount" or "therapeutically effective amount" refers to the amount of an active agent (such as one or more compounds provided herein alone, in combination, or potentially in combination with other therapeutic agent(s)) sufficient to induce a desired biological result. That result may be amelioration or alleviation of the signs, symptoms, or causes of a disease, or any other desired alteration of a biological system. The term "therapeutically effective amount" is used herein to denote any amount of a therapeutic that causes an improvement in a disease condition. The amount can vary with the condition being treated, the stage of advancement of the condition, and the type and concentration of formulation applied. Appropriate amounts in any given instance will be readily apparent to those of ordinary skill in the art or capable of determination by routine experimentation.

The term "pharmaceutically acceptable excipient" refers to a substance, other than the active ingredient, that is included in a formulation of the active ingredient. As used herein, an excipient may be incorporated within particles of a pharmaceutical composition, or it may be physically mixed with particles of a pharmaceutical composition. An excipient can be used, for example, to dilute an active agent and/or to modify properties of a pharmaceutical composition. Excipients can include, but are not limited to, solubilizing agents, antiadherents, binders, coatings, enteric coatings, disintegrants, flavorings, sweeteners, colorants, lubricants, glidants, sorbents, preservatives, adjuvants, carriers or vehicles. Excipients may be starches and modified starches, cellulose and cellulose derivatives, saccharides and their derivatives such as disaccharides, polysaccharides and sugar alcohols, polyesters, polyethylene glycol, protein, synthetic polymers, cross-linked polymers, antioxidants, amino acids or preservatives. Exemplary excipients include, but are not limited to, magnesium stearate, stearic acid, vegetable stearin, sucrose, lactose, starches, hydroxypropyl cellulose, hydroxypropyl methylcellulose, xylitol, sorbitol, maltitol, gelatin, polyvinylpyrrolidone (PVP), polyethyleneglycol (PEG), tocopheryl polyethylene glycol 1000 succinate (also known as vitamin E TPGS, or TPGS), carboxy methyl cellulose, dipalmitoyl phosphatidyl choline (DPPC), vitamin A, vitamin E, vitamin C, retinyl palmitate, selenium, cysteine, methionine, citric acid, sodium citrate, methyl paraben, propyl paraben, sugar, silica, talc, magnesium carbonate, sodium starch glycolate, tartrazine, aspartame, benzalkonium chloride, sesame oil, propyl gallate, sodium metabisulphite or lanolin.

An "adjuvant" is an excipient that modifies the effect of other agents, typically the active ingredient. Adjuvants are often pharmacological and/or immunological agents. An adjuvant may modify the effect of an active ingredient by increasing an immune response. An adjuvant may also act as a stabilizing agent for a formulation. Exemplary adjuvants include, but are not limited to, aluminum hydroxide, alum, aluminum phosphate, killed bacteria, squalene, detergents, cytokines, paraffin oil, and combination adjuvants, such as freund's complete adjuvant or freund's incomplete adjuvant.

The term "pharmaceutically acceptable carrier" refers to an excipient that is a carrier or vehicle, such as a suspension aid, solubilizing aid, or aerosolization aid. Pharmaceutically acceptable carriers are conventional. *Remington: The Science and Practice of Pharmacy*, The University of the Sciences in Philadelphia, Editor, Lippincott, Williams, & Wilkins, Philadelphia, Pa., $21^{st}$ Edition (2005), describes compositions and formulations suitable for pharmaceutical delivery of one or more therapeutic compositions and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The terms "proximal" and "distal" as used herein refer to distance from a site of administration of the disclosed composition. For example, proximal lymph nodes are lymph nodes that are close to the site of administration relative to an average distance of all lymph nodes to the site of administration. Similarly, distal lymph nodes are lymph nodes that are further away from the site of administration relative to the average distance of all lymph nodes to the site of administration.

I. Overview

Currently the FDA has 10 approved drugs for the treatment of metastatic melanoma based on inhibiting BRAF, mitogen-activated protein kinase, tyrosine kinase, or angiogenesis. The major drawback of the current therapy is the inability to deliver therapeutic concentrations to the lymphatic system while avoiding systemic toxicity. The majority of these inhibitors are administered intravenously (IV), resulting in high doses in the systemic circulation with an insufficient dose reaching the lymphatic vasculature. Secondarily, chemo-resistance has been noted for the approved drugs when used individually. Tumor cells are also known to induce resistance by up regulating alternate pathways when one of the pathways is blocked by specific inhibitors. Thus, there is a need for a combination therapy that can overcome drug resistance by acting on multiple pathways involved in melanoma as well as a drug delivery system that can be delivered into the lymphatic system.

Molecules and/or drug delivery systems accumulate in the lymphatics based on molecular weight, size, surface charge, and site of administration. A direct correlation between lymphatic absorption and molecular weight indicates that molecules with MW >16,000 Da preferentially accumulate into the lymphatics, while, the optimum particle size for lymphatic uptake is between 10-80 nm. Anionic charged particles have higher uptake compared to cationic or neutral particles, possibly due to the slight negative charge of the interstitium at the site of injection. The site of administration also plays a major role in delivering therapeutic payloads to the lymphatics where a higher accumulation of injected formulation in lymphatics is noted when injected subcutaneously (SC) as compared to the IV. As most chemotherapeutics for the treatment of melanoma are small molecules without the necessary properties for lymphatic uptake, a drug delivery system is needed to achieve the necessary lymphatic accumulation.

Figure 1B:
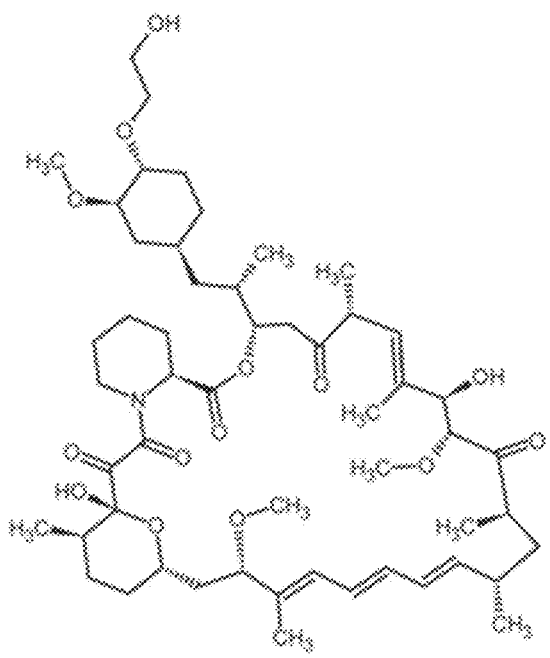
FIG. 1B shows the structure of everolimus (EVR).
Figure 1C:
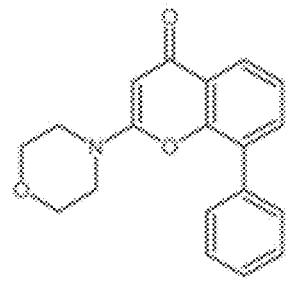
FIG. 1C shows the structure of experimental compound LY294002 (LY).

Chemotherapeutics like docetaxel (DTX), everolimus (EVR), and the experimental compound LY294002 (LY) are small molecules with MW ranging from 300 to a 1000 Da with low intrinsic aqueous solubility (FIGS. 1A-1C). Each of these molecules acts on different pathways to inhibit tumor proliferation: DTX acts by stabilizing the microtubules; and EVR and LY act on mammalian target of rapamycin, mTORC1 and mTORC2, respectively. Together, EVR and LY can completely inhibit the mTOR pathway while LY is also capable of inhibiting the Phosphoinositide 3-Kinase (PI3K) pathway. However, IV or SC administration of these molecules individually or together leads to systemic absorption with little accumulation in the lymphatic system.

Nanoparticles, prepared with amphiphilic block copolymers, are drug delivery systems that can be modified to target the lymphatic system. These block copolymers are comprised of hydrophilic and hydrophobic domains with varying chain lengths and different end groups that can be used to modulate nanoparticle size and charge density. Additionally, polyester-based polymers like polyethylene glycol-block-poly (ε-caprolactone) (PEG-PCL) are biodegradable and biocompatible. The nanoparticles formulated using these polymers have demonstrated excellent stability, increase the drug circulation time, and are capable of solubilizing poorly water soluble drugs while simultaneously delivering multiple drugs.

In some embodiments, a nanoparticle solution is formed by dissolving a suitable amount of a polymer, or mixture of polymers, in a solvent, or solvent mixture, suitable to facilitate the polymer or polymers forming nanoparticles. The amount of the polymer or polymers may be from greater than zero to 50 mgs or more polymer per mL of solvent, such as from 10 mgs to 40 mgs of polymer, or from 15 mgs to 30 mgs of polymer per mL of solvent, and in certain embodiments, about 20 mgs of polymer per mL of solvent are used.

Figure 2:
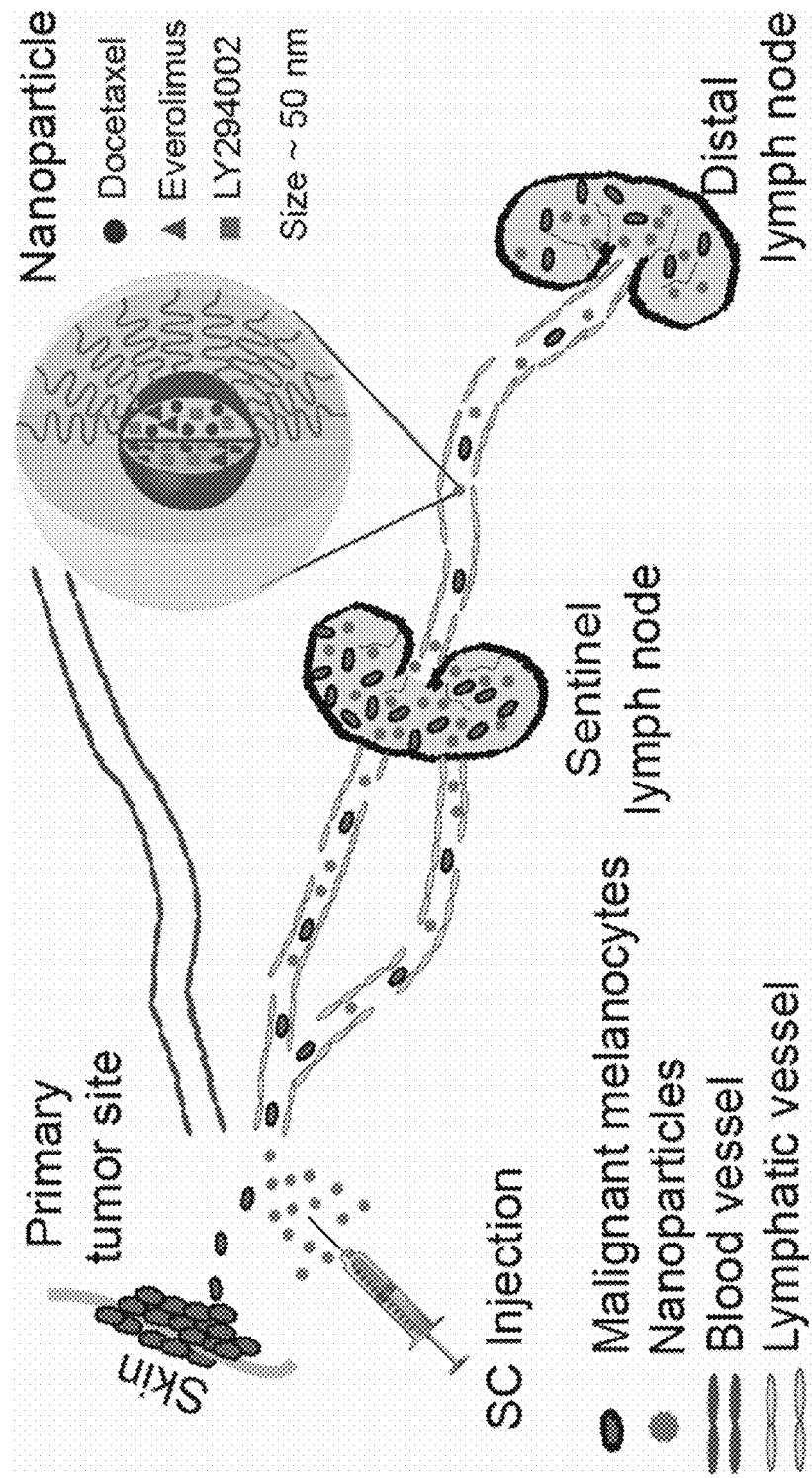
FIG. 2 is a schematic diagram showing how an exemplary three-drug-loaded nanoparticle may travel to the lymph nodes after injection.

Disclosed herein are embodiments of a composition comprising a drug in a nanoparticle drug delivery system. The drug may be docetaxel, everolimus, LY294002, paclitaxel, rapamycin, irinotecan, ixabepilone, vinblastine, vinorelbine, estramustine, vemurafenib, trametinib, dabrafenib or a combination thereof. Certain disclosed embodiments of the composition comprise docetaxel, everolimus, and LY294002, and certain other embodiments comprise trametinib and dabrafenib. The composition may overcome chemo-resistance issues that may be associated with the drugs if administered individually, and/or simultaneously targets the lymphatic system. The nanoparticle may be a PEG-PCL nanoparticle. The composition may be administered SC. Nanoparticle size and/or surface charge density is selected to provide preferential uptake and accumulation in the lymphatic system and/or dissemination throughout the lymphatic system, including to lymph nodes both proximal and distal to the site of administration. The composition may exert synergistic anti-proliferative effects in clinically relevant melanoma models (FIG. 2).

Figure 3:
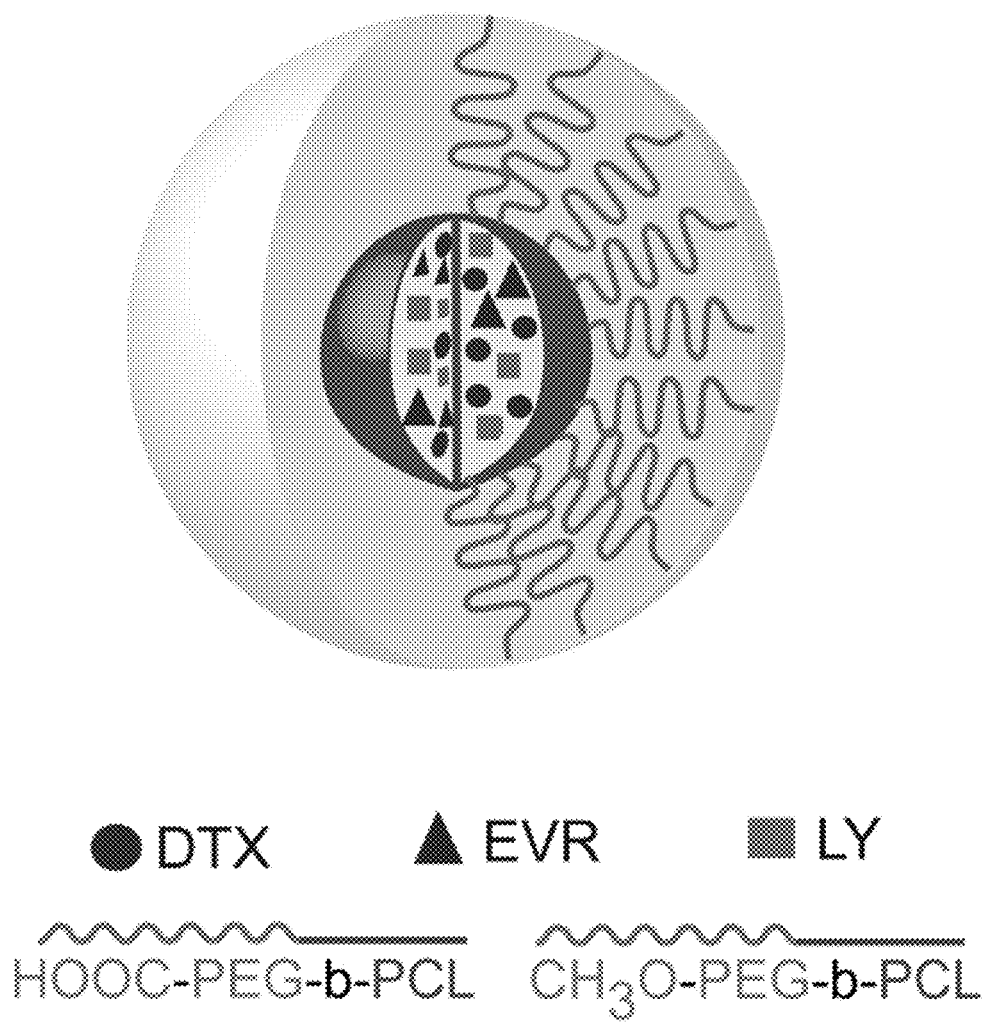
FIG. 3 is a schematic diagram illustrating the three drugs from FIGS. 1A, 1B and 1C loaded into a nanoparticle.

II. Results and Discussion
Preparation and Characterization of Three-Drug Loaded Nanoparticles Structures for the DTX, EVR, and LY along with a representation of a three-drug loaded nanoparticles are depicted in FIGS. 1 and 3. DTX, EVR, and LY neutral, partially charged, and fully charged nanoparticles were formulated by varying ratios of mPEG-PCL and COOH-PEG-PCL. These nanoparticles were similarly sized (about 50 nm), with neutral, partially charged, or fully charged surface. Based on the reverse-phase HPLC data, the three-drug neutral, partially charged, and fully charged nanoparticles were able to solubilize approximately 2 mg per mL of nanoparticle solution of each drug and retain each of the drugs at the initial concentrations (within 6%) for 24 hours (FIG. 4). The final molar ratios for the three drugs in the nanoparticles were 1:1:2 of DTX:EVR:LY. The intrinsic aqueous solubilities of DTX, EVR, and LY were 4 µg/mL, 9.6 µg/mL, and 243 µg/mL respectively. Thus, incorporation of these drugs into the nanoparticles increased the solubility of DTX, EVR, and LY by 455 fold, 201 fold and 8 fold respectively, thereby achieving therapeutically relevant dosing concentrations for in vivo assessment.

The particle sizes and polydispersity index (PDI) for the three-drug neutral, partially charged, and fully charged nanoparticles are presented in Table 1. The neutral, partially charged, and fully charged nanoparticles showed unimodal distribution as indicated with PDI values of less than 0.35. After 24 hours under either refrigeration or at room temperature, the size was re-assessed and no changes were seen in size or distribution (data not shown). No changes in the size over time are indicative of stability as no aggregation of the nanoparticles is occurring. Statistical analysis of the size distribution indicated that there was no significant difference between the particle sizes for neutral, partially charged, and fully charged nanoparticles. The mean zeta potential for neutral, partially charged, and fully charged nanoparticles are also presented in Table 1. The magnitude of the charge distribution correlated well with the increasing percentage of the negatively charged COOHPEG-PCL content in the nanoparticles.

Size and surface charge can affect the selective uptake of nanoparticles into the lymphatic system. Typically, such nanoparticles have a surface composition that facilitates uptake into the lymphatic system. In some embodiments, the nanoparticles have a surface comprising PEG units. PEG-PCL diblock copolymers produce nanoparticles of uniform size (around 50 nm) that selectively pass through the gaps in lymphatic endothelium (30-100 nm). Additionally, particles with a size above 20 nm accumulate into the lymphatics, however, when the particle size exceeds 100 nm the rate of particle drainage from the interstitum slows significantly. Thus, optimal particle sizes for interstitial drainage and lymphatic accumulation are between 20-80 nm. Accordingly, the drug loaded PEG-PCL nanoparticles disclosed therein, with an average size of 47 nm, preferentially accumulate into the lymphatics. With respect to surface charge, anionic nanoparticles have a higher uptake into lymphatic vessels when compared to their neutral and cationic counterparts. Other studies have indicated that highly negative charged particles can trigger macrophage uptake. Therefore, a differential accumulation of the nanoparticles in the lymph nodes in vivo occurs based on the surface charge distribution. Additionally, as all of the nanoparticles have similar sizes any differences in lymphatic uptake can be attributed to the difference in surface charge alone. In some embodiments, the nanoparticles have a zeta potential of from −1 mV to −30 mV, such as from −10 mV to −20 mV.

TABLE 1

Particle Size, PDI, and Zeta potential values for three-drug neutral, partially charged and fully charged nanoparticles (NP)

(Mean ± SD, n = 3)

| | Mean Size ± SD (nm) | PDI ± SD | Mean Zeta Potential (ζ) ± SD (mV) |
|---|---|---|---|
| Neutral NP | 48.08 ± 0.31 | 0.31 ± 0.01 | −0.64 ± 0.24 |
| Partially charged NP | 48.30 ± 0.42 | 0.25 ± 0.01 | −19.2 ± 2.15 |
| Fully charged NP | 48.60 ± 0.66 | 0.31 ± 0.02 | −37.6 ± 1.02 |

TABLE 2

Fast and slow half-lives ($t_{1/2}$) and goodness of fit ($r^2$) values of DTX, EVR, and LY in neutral, partially charged, and fully charged nanoparticles (NP) using a two phase association curve fitting.

| | | Fast $t_{1/2}$ | Slow $t_{1/2}$ | $r^2$ |
|---|---|---|---|---|
| Neutral NP | DTX | 0.86 | 28.19 | 0.9735 |
| | EVR | 0.39 | 3.67 | 0.9093 |
| | LY | 0.52 | 7.73 | 0.9919 |
| Partially charged NP | DTX | 0.61 | 22.68 | 0.9756 |
| | EVR | 0.43 | 4.46 | 0.9481 |
| | LY | 0.44 | 10.66 | 0.9925 |
| Fully charged NP | DTX | 0.80 | 24.44 | 0.9814 |
| | EVR | 0.32 | 5.49 | 0.9700 |
| | LY | 0.34 | 6.93 | 0.9927 |

In Vitro Drug Release from the Nanoparticles

Figure 5:
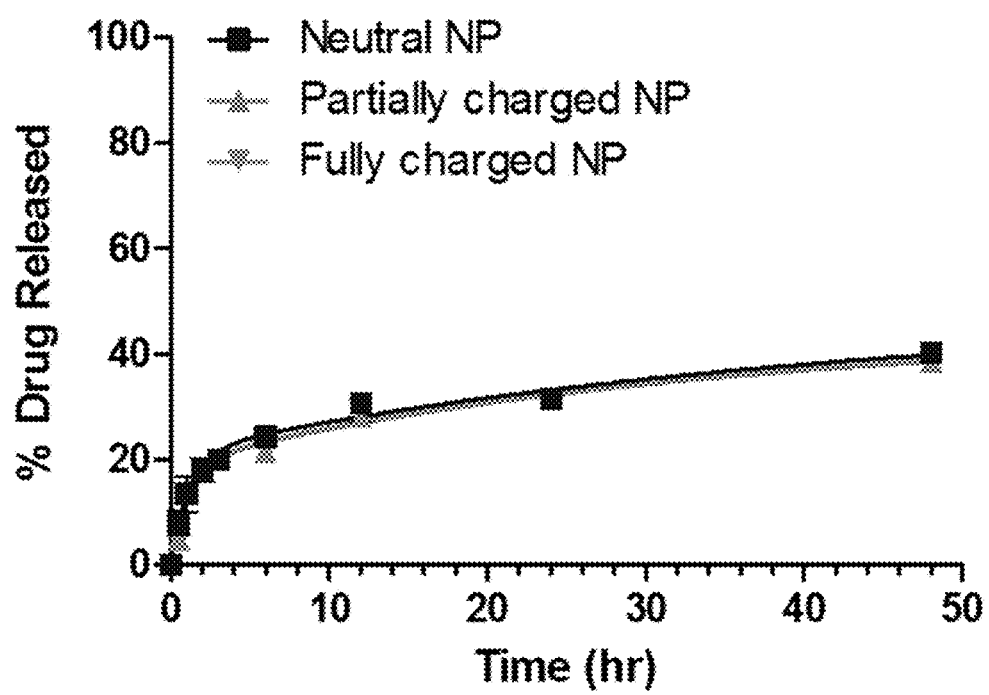
FIG. 5 is a graph of drug released versus time illustrating the in vitro drug release profile of DTX from neutral, partially charged, and fully charged nanoparticles in phosphate buffer at pH 7.4 under sink conditions over 48 hours.
Figure 6:
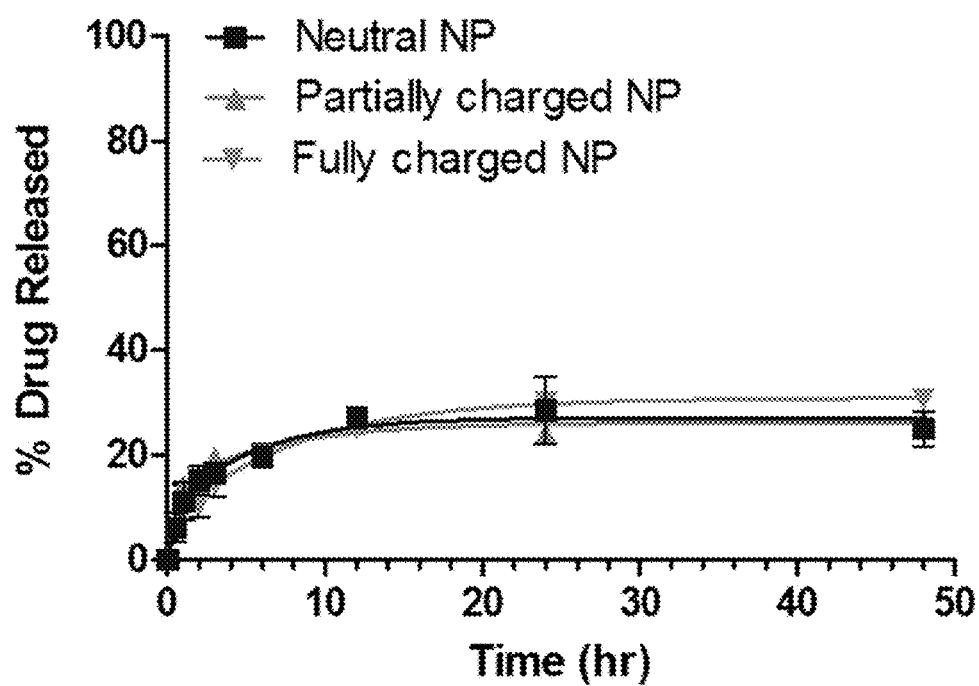
FIG. 6 is a graph of drug released versus time illustrating the in vitro drug release profiles of EVR from neutral, partially charged, and fully charged nanoparticles in phosphate buffer at pH 7.4 under sink conditions over 48 hours.
Figure 7:
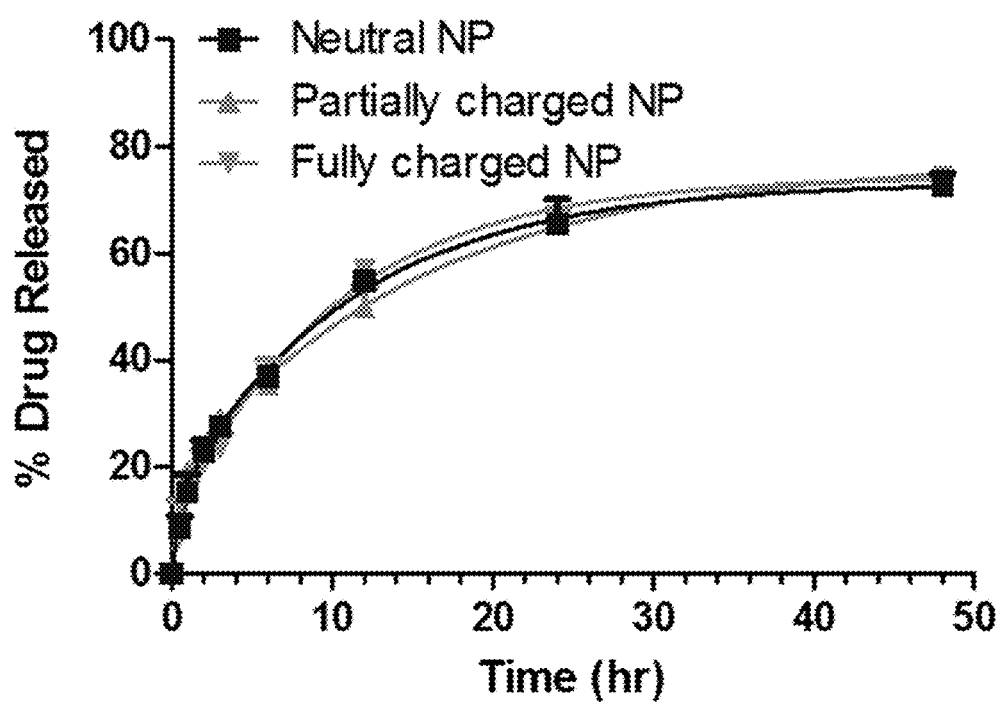
FIG. 7 is a graph of drug released versus time illustrating the in vitro drug release profiles of LY from neutral, partially charged, and fully charged nanoparticles in phosphate buffer at pH 7.4 under sink conditions over 48 hours.

The release profiles of DTX, EVR and LY from the three-drug neutral, partially charged, and fully charged nanoparticles are shown in FIGS. 5-7. The release of DTX from neutral, partially charged, and fully charged nanoparticles was 40.22±1.41%, 38.62±0.61%, and 39.60±1.47% respectively (FIG. 5). For EVR (FIG. 6), release from the neutral, partially charged, and fully charged nanoparticles was 25.00±3.27%, 27.20±0.31%, and 30.69±1.69% respectively. LY release from neutral, partially charged and fully charged nanoparticles was 72.95±2.00%, 74.40±1.54%, and 74.50±0.22% respectively (FIG. 7). The highest percentage release occurred with LY, followed by DTX, and then EVR. Overall, there was no significant difference in the rates of drug release for each drug from nanoparticles of different compositions. The release profile of DTX, EVR and LY from the neutral, partially charged, and fully charged nanoparticles was almost identical to similar half-life values. The two phase exponential association $t_{1/2}$ and $r^2$ values for DTX, EVR, and LY release from the neutral, partially, and fully charged nanoparticles are presented in Table 2. As seen in FIGS. 5-7, there was an initial phase involving burst/rapid release of the drugs from the nanoparticles followed by a more sustained release pattern at later stages. Without being bound to a particular theory, the initial burst release may be primarily driven by the desorption and the diffusion of surface adsorbed drug particles, while the secondary phase of drug release may be driven by the erosion of the nanoparticle matrix and drug diffusion processes. The inner segment, PCL, is a biodegradable polyester that has a high crystallinity while the outer PEG shell increases the porosity in the PCL matrix and thereby allows the diffusion of drugs from the matrix into the buffer. Thus, drug release is governed by diffusion of the drug and erosion/degradation of the nanoparticle matrix. Previous studies have demonstrated that solid state interactions between the drug and the hydrophobic block, and the mobility of the hydrophobic block all govern the drug release rate. LY had the fastest drug release from the three-drug nanoparticles followed by DTX and then EVR. This may be due to the relative hydrophobicities of these molecules and their potential interaction with the PCL domain. The log D values at pH 7.4 for LY, DTX and EVR are 3.33, 3.54, and 4.25 respectively (Advanced Chemistry Development ACD/Universal LogD Module, Percepta 14.0.0 (Build 1996)).

In Vitro Cell Viability Assay and Combination Index (CI) Analysis

Figure 8:
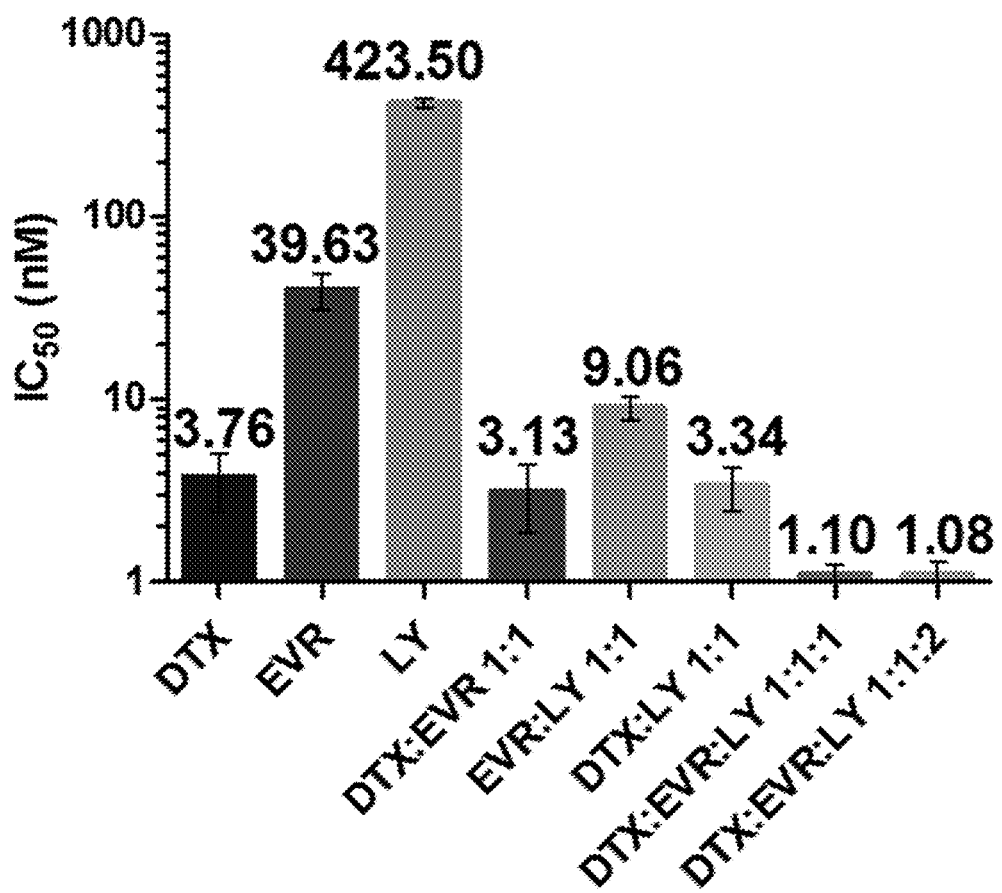
FIG. 8 is a graph of $IC_{50}$ versus drug regime illustrating the mean $IC_{50}$ values for DTX, EVR, LY, two- and three-drug combinations in DMSO in A375 metastatic melanoma cells.

The anti-proliferative effects ($IC_{50}$ values) of DTX, EVR, and LY in DMSO individually and in two- and three-drug combinations evaluated in A375 human melanoma cells are presented in FIG. 8. The two-drug combinations (1:1 molar ratio) and the three-drug combinations (1:1:1 or 1:1:2 molar ratios) in DMSO exhibited strong inhibition of A375 cell proliferation over a wide range of tested doses. As the prepared nanoparticles were at 1:1:2 molar ratio of DTX:EVR:LY, the 1:1:2 ratio of these drugs was also evaluated for anti-proliferative effects in the cell line. Based on the data (FIG. 8) the two- and three-drug combinations were more potent than the individual drug treatments, with the three-drug combination, at both ratios, demonstrating the highest potency at approximately 1 nM concentration. The DTX:EVR:LY neutral, partially charged, or fully charged nanoparticles were also evaluated in A375 cells to determine their respective $IC_{50}$ values. The $IC_{50}$ values for the three-drug neutral, partially charged, and fully charged nanoparticles were 38.19±0.60 nM, 31.227±5.96 nM, and 9.17±0.93 nM respectively. The $IC_{50}$ values were higher in the nanoparticles due to entrapment and non-sink conditions in the cell culture experiments. While the neutral and partially charged nanoparticles had similar $IC_{50}$ values, the fully charged nanoparticles were more potent. The higher potency of the fully charged particles may be due to the high surface potential which can be toxic to cells.

Figure 9:
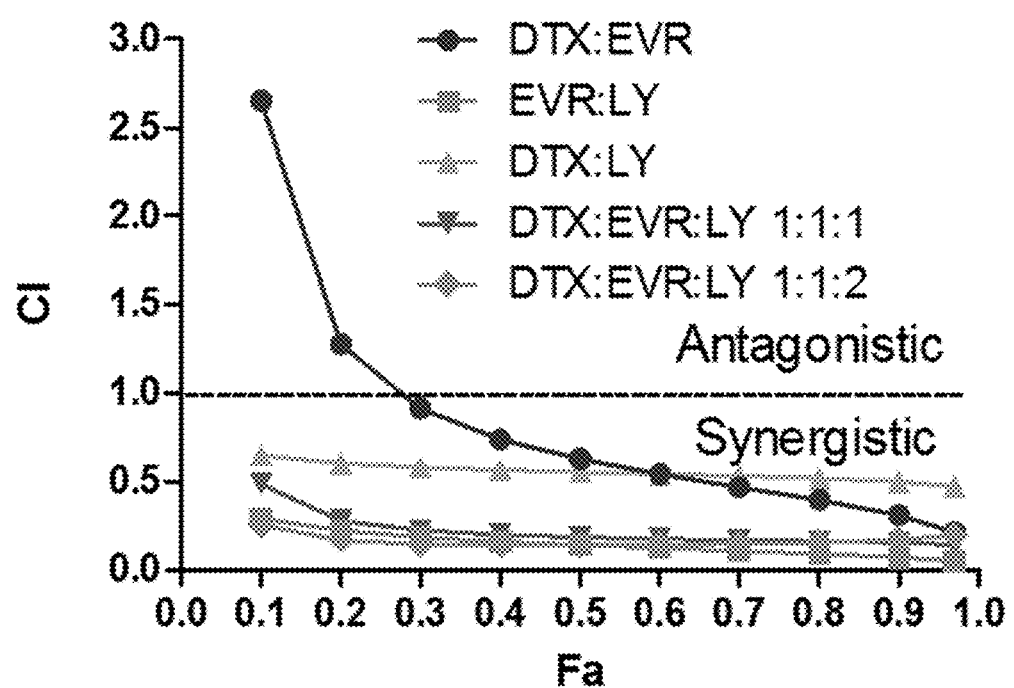
FIG. 9 is a graph of combination index (CI) versus fractions of cells affected (Fa) for the two- and three-drug combinations in A375 metastatic melanoma cells.
Figure 10A:
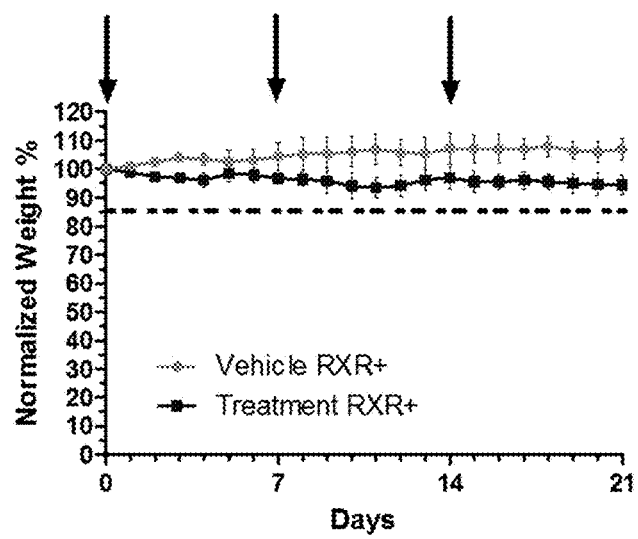
FIGS. 10A to 10F are graphs of normalized weight % versus days illustrating the normalized body weight of mice injected subcutaneously with empty or three drug nanoparticles in Tyr Nras$^{Q61K}$ RXRα$^{L2/L2}$ (RXR+) (10A, 10B, and 10C) and Tyr Nras$^{Q61K}$ RXRα$^{ep-/-}$ (RXR−) (10D, 10E, and 10F) mice.
Figure 10B:
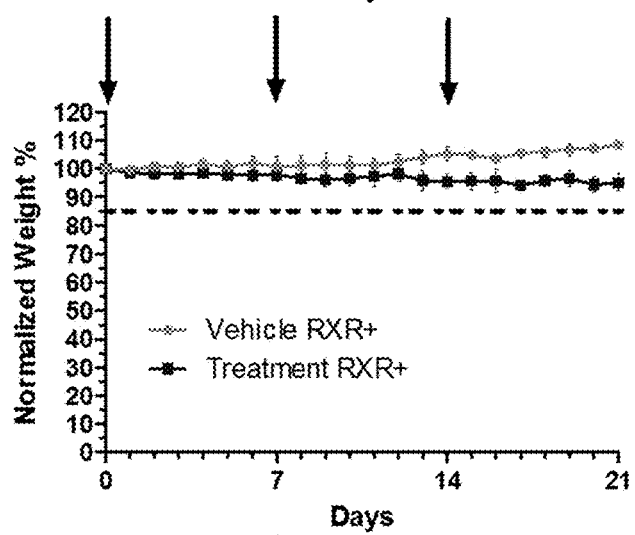
Figure 10C:
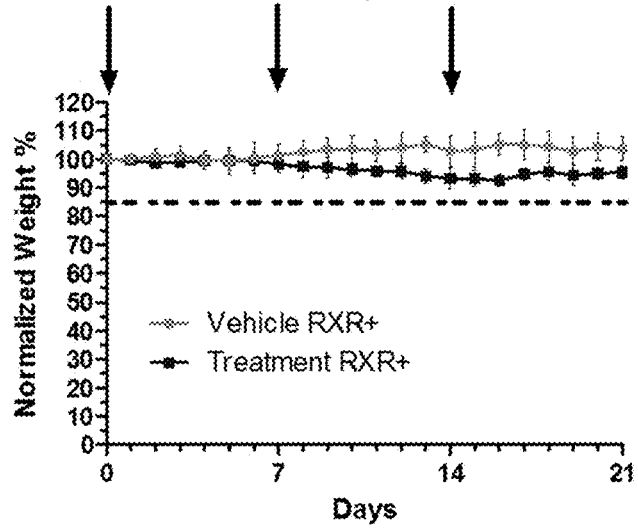
Figure 10D:
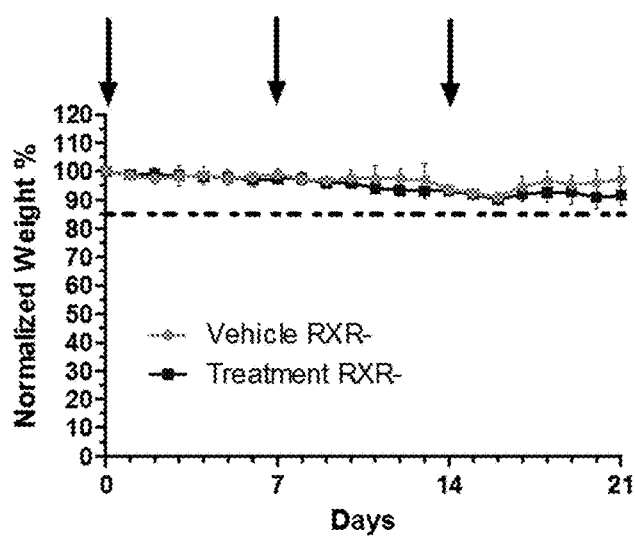
Figure 10E:
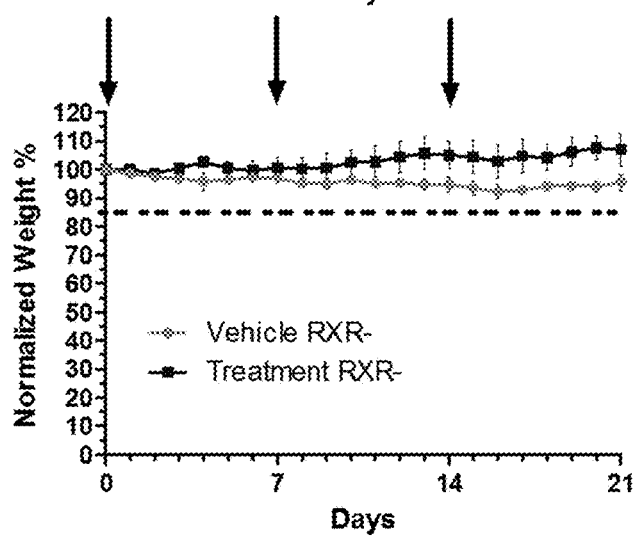
Figure 10F:
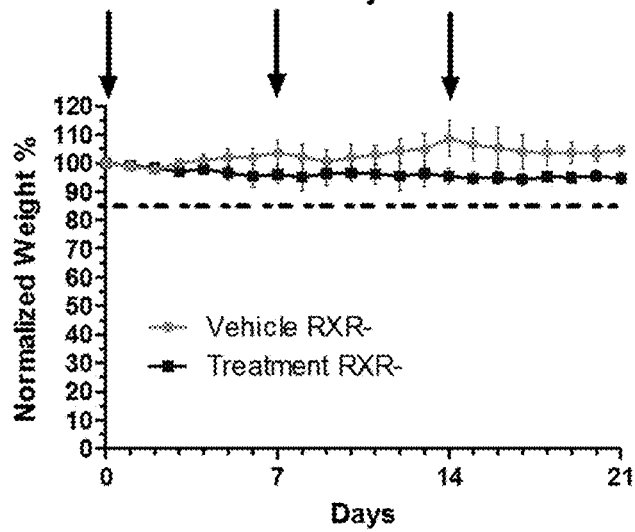

The two- and three-drug combinations were also evaluated for interactive effects (synergistic, additive, or antagonistic) using Compusyn software and the data are presented in FIG. 9. The two-drug combination DTX:EVR appeared synergistic at higher concentrations but antagonistic at lower concentrations. The EVR:LY and DTX:LY combinations were synergistic at all concentrations as (FIG. 9). The three-drug combination was also synergistic at all the fractions affected, indicating that the multiple mechanisms of action enhanced the potency of the combination beyond what was expected with individual drug treatments alone. While the EVR:LY combination was as synergistic as both the three-drug combinations (FIG. 9), the three-drug combination exhibited greater potency with a lower $IC_{50}$ value (FIG. 8). Therefore, for the in vivo studies the three-drug combination at 1:1:2 in nanoparticles was used as this was the molar ratio of the drugs in the nanoparticle.

The three-drug combination may have achieved these synergistic effects by blocking multiple pathways involved in cancer progression. Cancer cells up regulate alternative mechanisms to induce drug resistance when one particular pathway is blocked. The mTOR pathway is involved in cell growth, proliferation, and survival, and in addition it affects downstream effector proteins which are essential for the protein translation processes. It has been reported previously that the mTOR pathway is highly up regulated in malignant melanoma, and inhibiting the mTOR pathway can have beneficial effects in the treatment regimen. EVR acts on the mTOR1 pathway and it is known that the cancer cells immediately up regulate the mTOR2 pathway to induce drug resistance when the mTOR1 pathway is blocked. LY targets the mTOR2 pathway and also blocks the PI3K/AKT pathway. Thus, when LY is used in combination with EVR the mTOR cascade may be completely blocked. DTX acts by a different mechanism where it stabilizes the microtubules and thereby induces apoptosis. Thus, the combination of these three drugs can synergistically inhibit proliferation through multiple mechanisms of action as evidenced by the potency and CI for the three-drug combination as compared to individual drugs or the two-drug combinations.

In Vivo Assessment of Safety and Efficacy in Tyr NRAS$^{Q61K}$ RXR$\alpha^{L2/L2}$ and Tyr NRAS$^{Q61K}$ RXR$\alpha^{ep-/-}$ Metastatic Melanoma Mouse Models The safety profile of the neutral, partially charged, and fully charged nanoparticles was evaluated in two metastatic melanoma mouse models containing activating NRAS$^{Q61K}$ driver mutation and with or without RXR α-protein (RXR+ or RXR−), which develop melanoma with different latency and with lymph node (LN) metastasis as described elsewhere. None of the mice in either model died or exhibited abnormal behavioral changes during the duration of the study. Changes in the weight, during the course of the study, for the neutral, partially charged, and fully charged nanoparticles, with or without the three drugs are presented in FIG. 10. FIGS. 10A-10F show neutral nanoparticles in RXR+ (FIG. 10A) and RXR− (FIG. 10D), partially charged nanoparticles in RXR+ (FIG. 10B) and RXR− (FIG. 10E) mice, and fully charged nanoparticles in RXR+ (FIG. 10C) and RXR− (FIG. 10F) mice. The mice were injected at a dose of 20 mg/kg for each drug in the treatment group and 20 mg/kg of the polymer in all groups. The arrows indicate the days of injection (0, 7, and 14). The dashed line depicts the threshold weight loss of 15% which is indicative of acute toxicity. Based on the data, none of the groups in either model demonstrated weight loss ≥15% indicating that neither the empty nanoparticles nor the three-drug nanoparticles produced acute toxicity at 20 mg/kg dose of each drug (total 60 mg/kg dose) and 20 mg/kg of the nanoparticle polymer.

Figure 11:
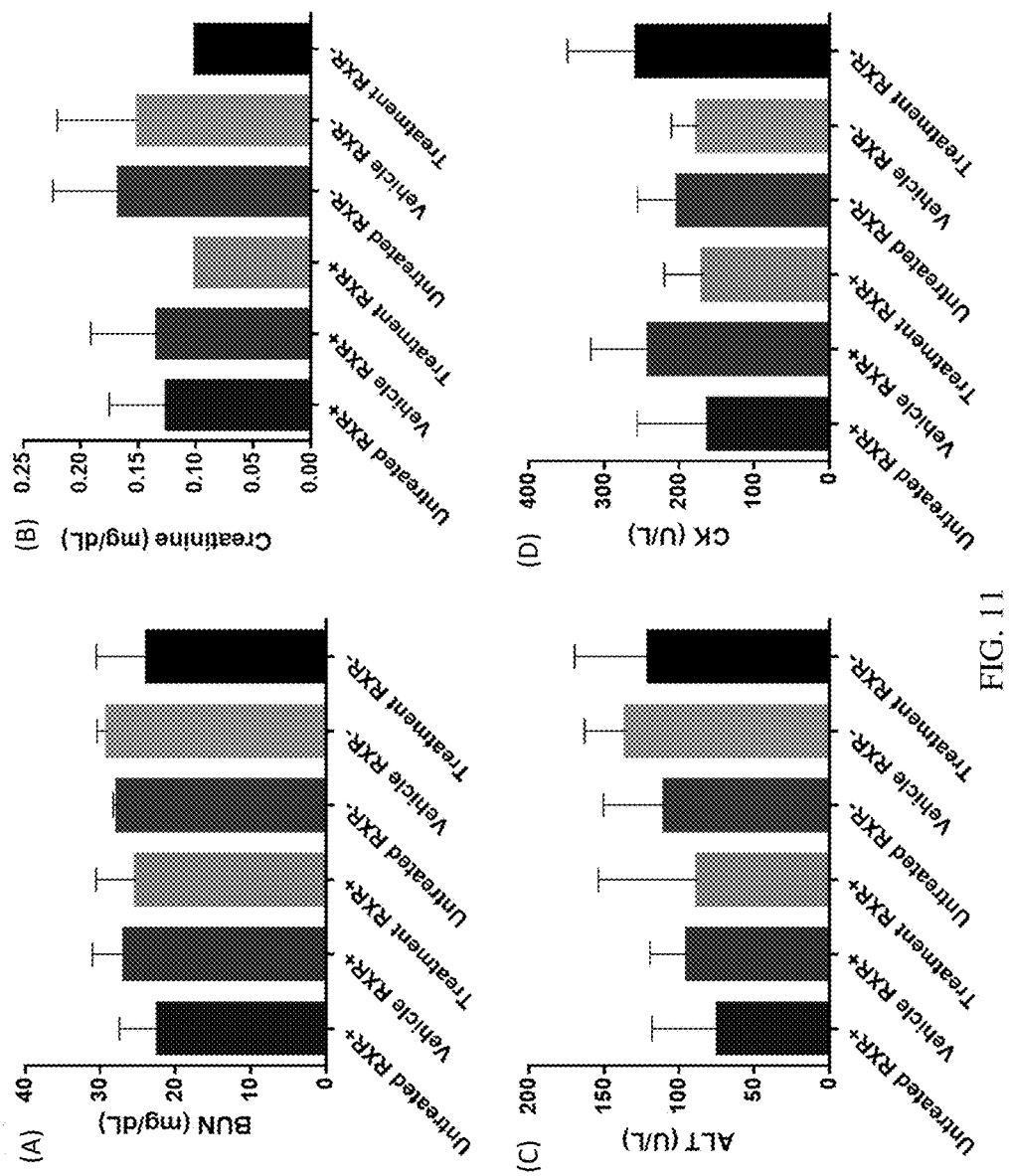
FIGS. 11A to 11D are graphs showing BUN (11A), Creatinine (11B), ALT (11C), and CK (11D) values from mice injected subcutaneously with the empty neutral nanoparticles or three-drug neutral nanoparticles in Tyr NRASs$^{Q61K}$ RXRα$^{L2/L2}$ (RXR+) and Tyr NRAS$^{Q61K}$ RXRα$^{ep-/-}$ (RXR−) mice.
Figure 12:
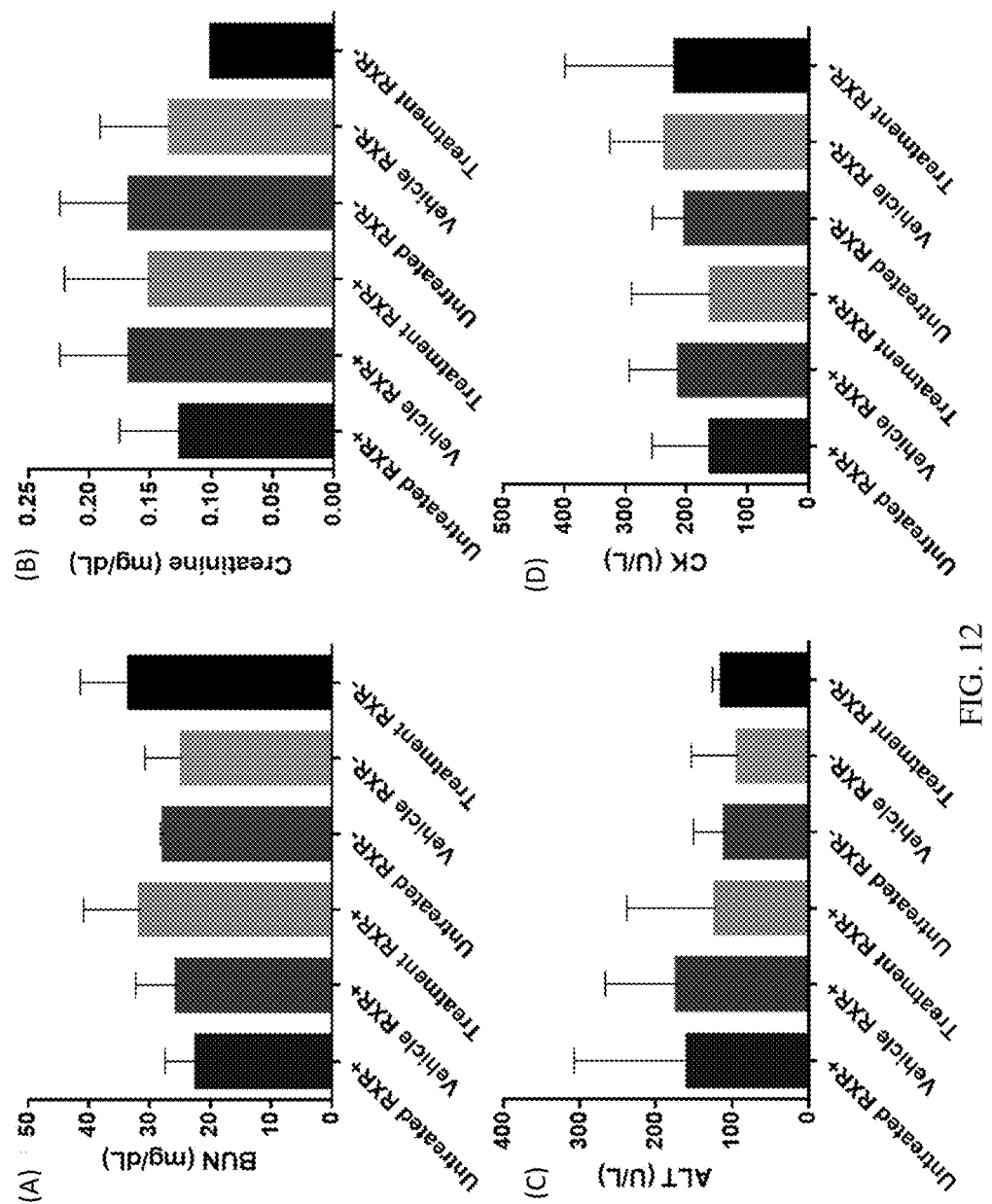
FIGS. 12A to 12D are graphs showing BUN (12A), Creatinine (12B), ALT (12C), and CK (12D) values from mice injected subcutaneously with the empty partially charged nanoparticles or three-drug partially charged nanoparticles in Tyr NRASs$^{Q61K}$ RXRα$^{L2/L2}$ (RXR+) and Tyr NRAS$^{Q61K}$ RXRα$^{ep-/-}$ (RXR−) mice.
Figure 13:
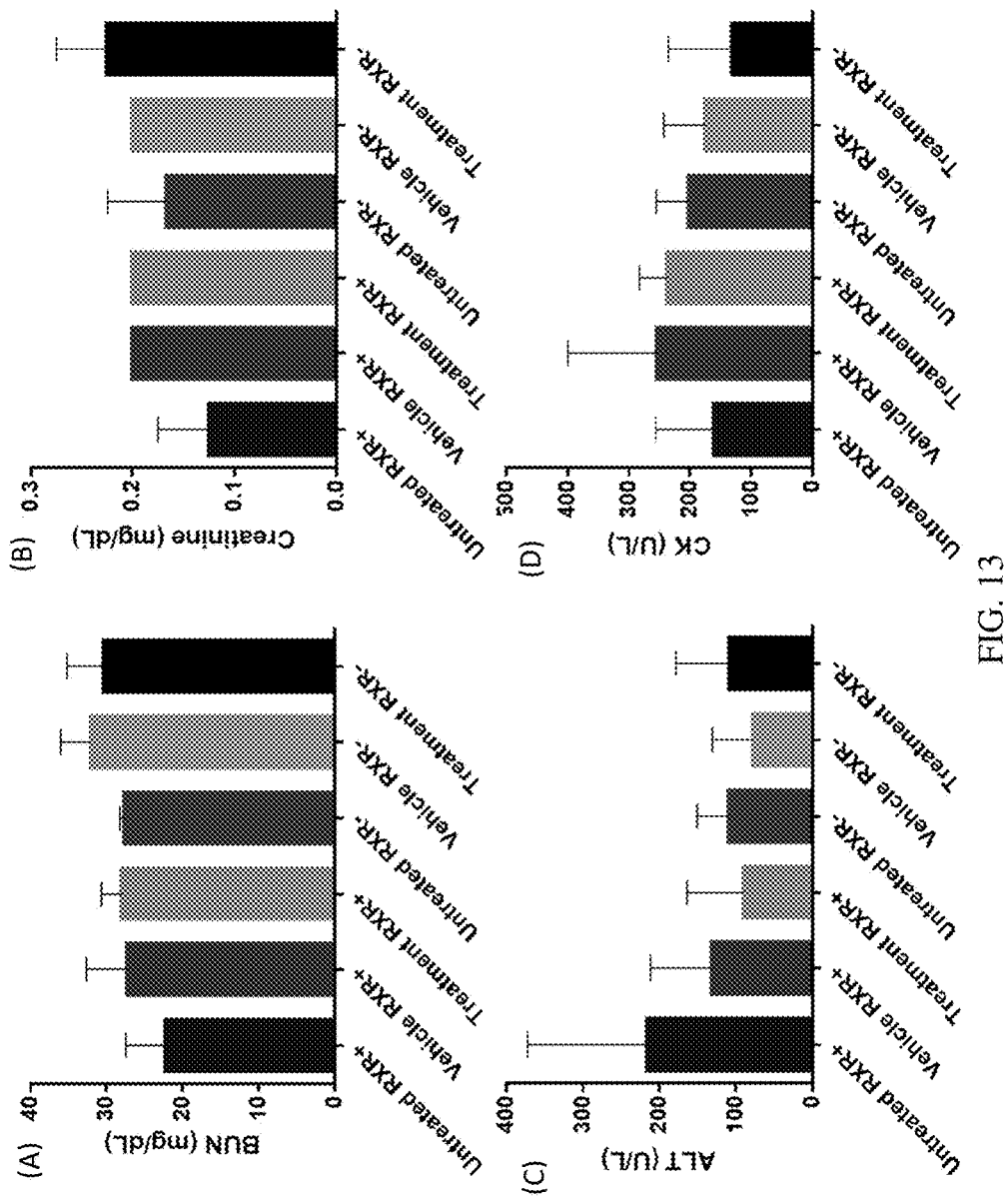
FIGS. 13A to 13D are graphs showing BUN (13A), Creatinine (13B), ALT (13C), and CK (13D) values from mice injected subcutaneously with the empty fully charged nanoparticles or three-drug fully charged nanoparticles in Tyr NRASs$^{Q61K}$ RXRα$^{L2/L2}$ (RXR+) and Tyr NRAS$^{Q61K}$ RXRα$^{ep-/-}$ (RXR−) mice.

The values of blood biochemical parameters for BUN, Creatinine, ALT, and CK values for all the groups in each model are presented in FIGS. 11-13. With reference to FIGS. 11A-11D, BUN (A), Creatinine (B), ALT (C), and CK (D) values in RXR+ and RXR− treated with empty neutral or three-drug neutral nanoparticles indicated that there were no statistically significant differences between the treatment groups and the untreated and vehicle controls. Similar results were seen with the partially charged (FIGS. 12A-12D) and fully charged (FIGS. 13A-13D) nanoparticle groups. One way ANOVA with Tukey's Multiple Comparison tests were used for statistical analysis at p-value of 0.05.

BUN, and creatinine levels are indicators of kidney function. In cases of renal toxicity, levels of BUN and/or creatinine are elevated. ALT is present in all tissues throughout the entire body, but is particularly concentrated in liver, bile duct, kidney, and bone. Elevated ALT levels are usually indicative of liver toxicity. CK is an enzyme found in the heart, brain, skeletal muscle, and other tissues and elevated levels of CK are indicative of muscle damage and/or rhabdomylosis in the liver. Based on the behavioral observations, weight data (FIGS. 10A-10F), and the biochemical estimations (FIGS. 11-13) no acute toxicity was observed with either the empty or three-drug loaded nanoparticles.

The effectiveness of the treatment in the two different models of metastatic melanoma mouse models was established using Fontana Masson (FM) staining of the LN followed by quantification of pigment areas covered with invading melanocytes in the draining LN using Adobe Photoshop CS5 software. The melanocyte covered pigmented area (black stain) between the empty nanoparticles and the three-drug nanoparticles for the same charge distribution were compared to quantify the efficacy, in terms of decrease in the number of invasive, malignant melanocytes in the LNs.

Figure 14:
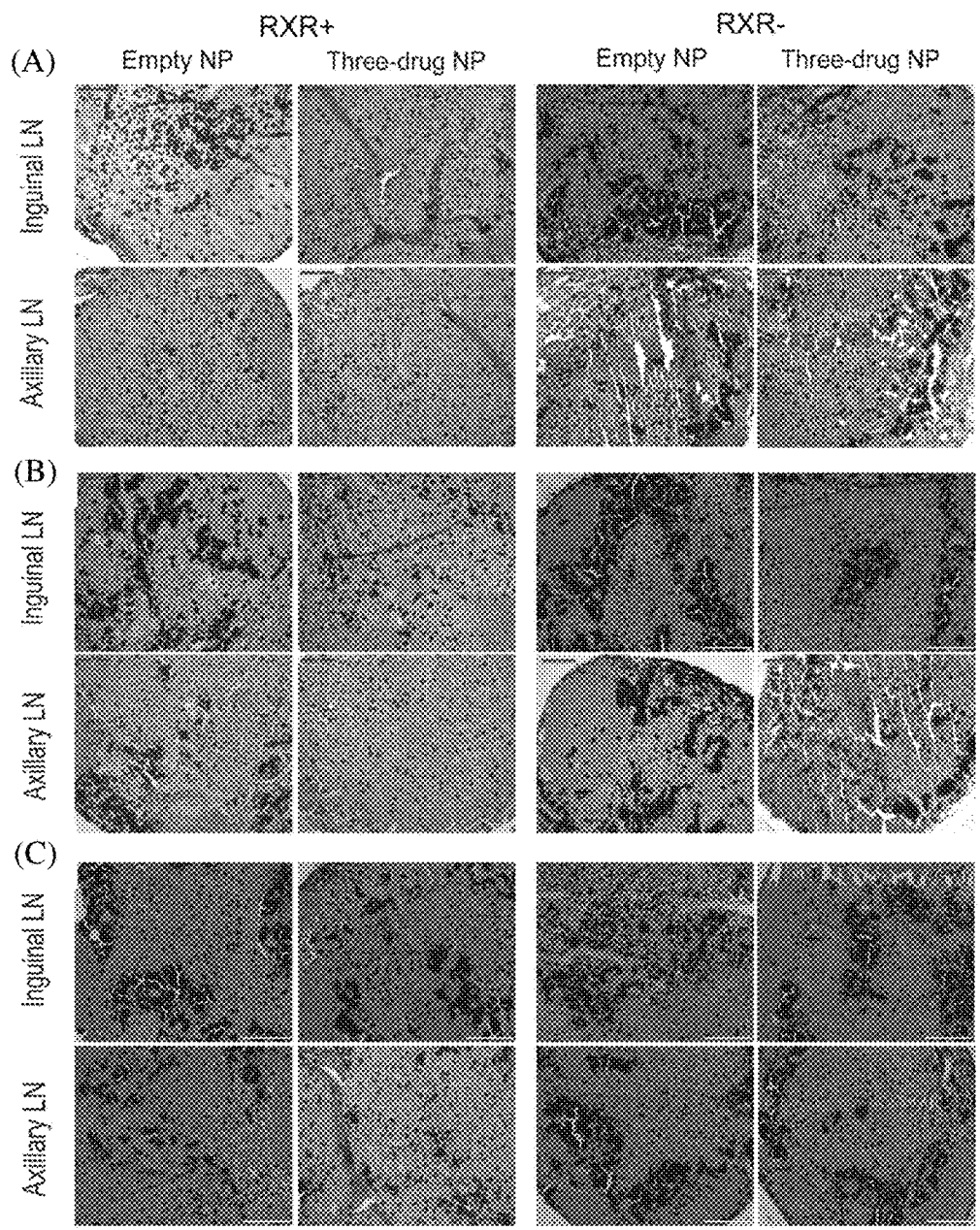
FIGS. 14A to 14C are photographs of Fontana-Masson (FM) staining of lymph node sections after treatment with the empty or three-drug nanoparticles in Tyr NRAS$^{Q61K}$ RXRα$^{L2/L2}$ (RXR+) and Tyr NRAS$^{Q61K}$ RXRα$^{ep-/-}$ (RXR−) mice.

A representative microscopic data set from the inguinal and axillary LN is presented in FIG. 14 for RXR+ and RXR− mice treated with neutral, partially charged, and fully charged empty or three-drug nanoparticles. With reference to FIG. 14, FIG. 14A shows neutral nanoparticles in RXR+ and RXR− mice, FIG. 14B shows partially charged nanoparticles in RXR+ and RXR− mice, and FIG. 14C shows fully charged nanoparticles in RXR+ and RXR− mice. The mice were injected at a dose of 20 mg/kg for each drug in the treatment group and 20 mg/kg of the polymer in all groups on days 0, 7, and 14. The scale bar represents 100 μm. The reduction in the transformed melanocytes covered pigmented area was dependent on the uptake and trafficking of the differently charged nanoparticles in the lymphatic system. As seen in FIG. 14A with three-drug neutral nanoparticles as compared to empty neutral nanoparticles a reduction in melanocytes area in the inguinal LN (proximal to the injection sites) was seen in both models (RXR+ and RXR−). However, no change in pigmented melanocytes area was noted in the axillary LN (distal from the injection sites), indicating that the efficacy of the drug loaded neutral particles was limited to the inguinal LN in both models. Analysis of melanocyte covered pigmented area indicated a statistically significant difference (p=0.0003) at the inguinal LN of both the RXR+ and RXR− groups (see FIGS. 15A and 15B) but no difference was observed at the axillary LN. One possible explanation is that the nanoparticles remained at the site of injection after dosing and showed efficacy only at the proximal inguinal LN. One of the ways by which particles traffic into the lymphatic system is through charge repulsion between the nanoparticles and the interstitium at the site of injection. For the neutral nanoparticles the magnitude of the surface charge may not be large enough to induce electrostatic repulsions to allow for distal trafficking through the lymphatics. Additionally, studies by others have shown that neutral nanoparticles may aggregate at the site of injection, which may also inhibit the particles from tracking distally into the lymphatics, but show efficacy regionally.

Figure 15A:
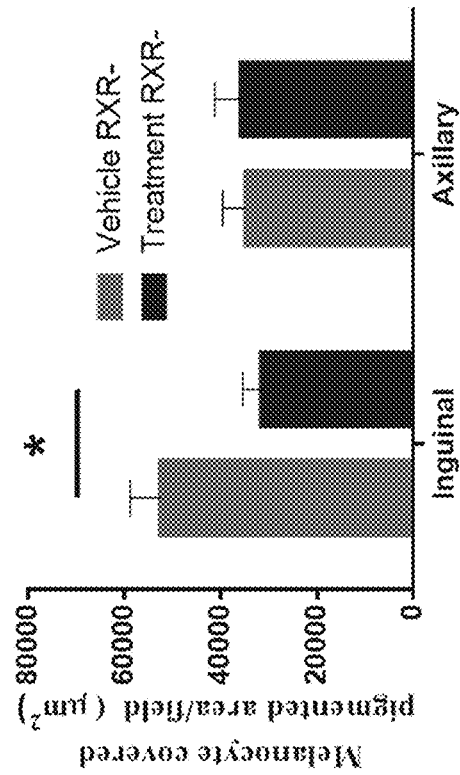
FIGS. 15A to 15F are graphs of melanocyte covered pigmented area per field versus treatment for Tyr NRAS$^{Q61K}$ RXRα$^{L2/L2}$ (RXR+) and Tyr NRAS$^{Q61K}$ RXRα$^{ep-/-}$ (RXR−) negative mice treated with empty or three-drug nanoparticles.
Figure 15B:
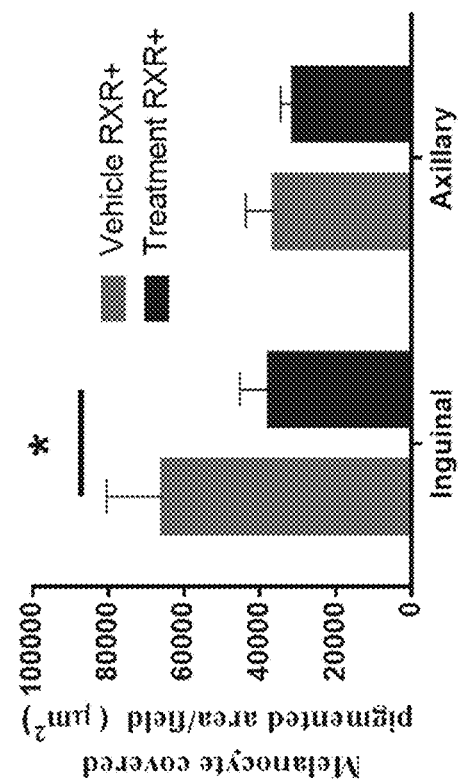
Figure 15C:
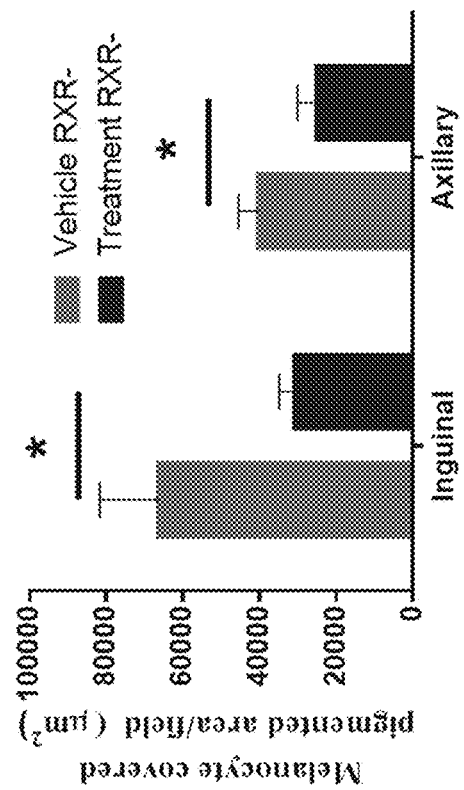
Figure 15D:
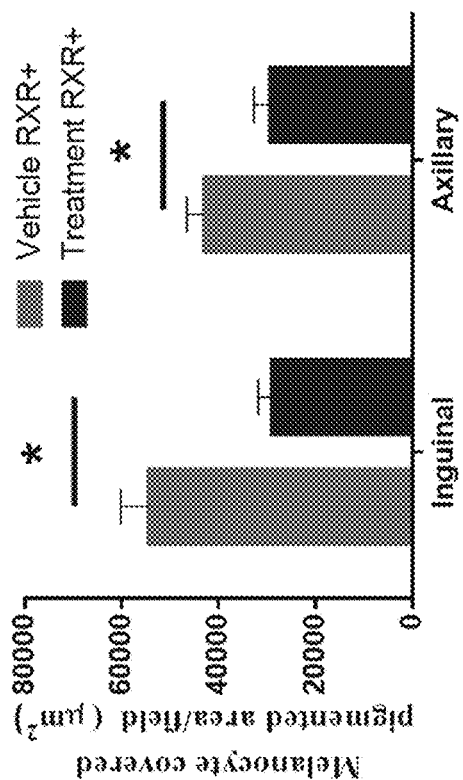
Figures 15E, 15F:
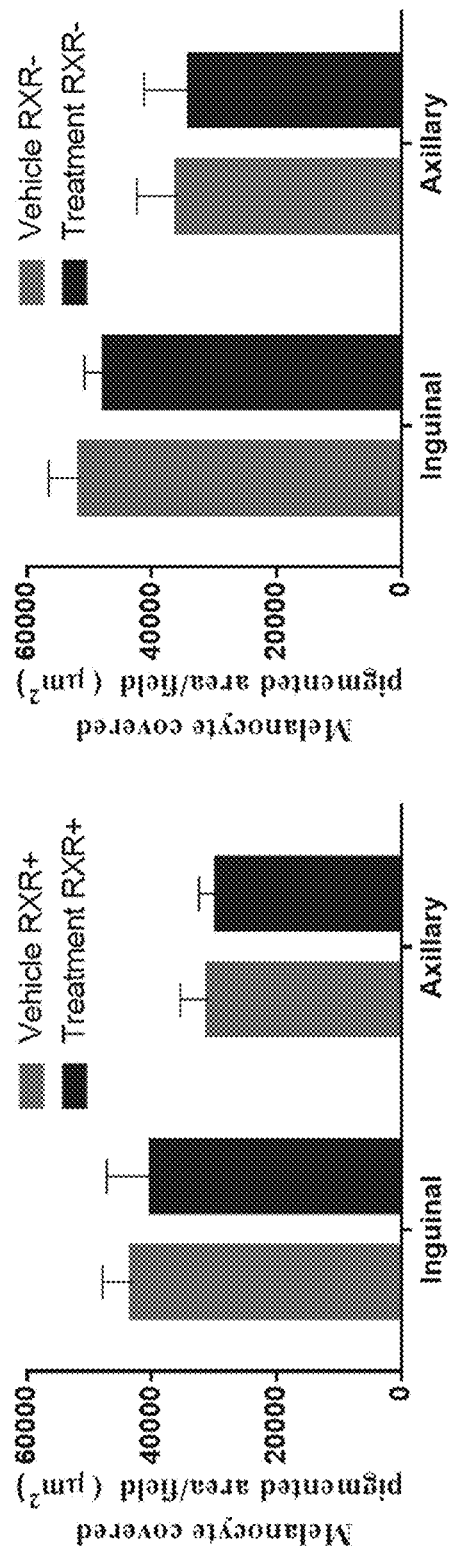

In comparing the three-drug partially charged nanoparticles with empty partially charged nanoparticles (FIG. 14B), a decrease in melanocytes at both the inguinal and the axillary LN in both models was noted. These results indicated that the three-drug partially charged nanoparticles were efficacious at both the proximal (inguinal) and distal (axillary) LN as referenced from the site of injection for both the models. FIG. 15 provides the mean melanocytic pigmented area per field (μm$^2$) treated with empty or three-drug nanoparticles in Tyr NRAS$^{Q61K}$ RXR$\alpha^{L2/L2}$ (RXR+) and Tyr NRAS$^{Q61K}$ RXR$\alpha^{ep-/-}$ (RXR−) negative mice. FIGS. 15A and 15B show neutral nanoparticles in RXR+ and RXR− mice, respectively; FIGS. 15C and 15D show partially charged nanoparticles in RXR+ and RXR− mice, respectively; and FIGS. 15E and 15F show fully charged nanoparticles in RXR+ and RXR− mice, respectively. The mice were injected at a dose of 20 mg/kg for each drug in the treatment group and 20 mg/kg of the polymer in all groups on days 0, 7, and 14. Values are expressed as a mean±SEM (n=4), and * indicates statistical significance as determined by a Student's two-tailed unpaired t-test with a p-value of 0.05.

Analysis of melanocyte covered pigmented area indicated a statistically significant difference at both the inguinal (p<0.0001) and the axillary (p<0.0001) LN in both the mouse models upon treatment with the three-drug partially charged nanoparticles (FIGS. 15C and 15D). The lymphatic vessels and the interstitium have a slight negative charge because of the presence of glycosaminoglycans, and the electrostatic repulsions between these and the partially charged nanoparticles (surface charge of −19 mV) may be responsible for the deeper movement of the particles into the lymphatic system. The ability of these nanoparticles to track into the distal LN provides an excellent opportunity to target advanced stages of metastatic melanoma and improve patient outcomes.

Comparing the staining in empty fully charged and three-drug fully charged nanoparticles (FIG. 14C), no difference at either the inguinal or the axillary LN was observed in both models. Therefore, the fully charged nanoparticles did not have an appreciable accumulation in either of the two LN studied. Analysis of melanocyte covered pigmented area indicates no difference between empty and three-drug fully charged nanoparticles at both the inguinal and axillary LN in both models (FIG. 15E and 15F). The data indicated that highly negatively charged particles did not tract into either the regional or distal LN (FIGS. 14C, 15E and 15F).

Two different animal models were used in this study, containing mutations in NRAS and/or RXRα to elucidate the effectiveness of the disclosed drug delivery system, and also to characterize the efficacy and toxicity of the formulated nanoparticles. The Tyr NRAS$^{Q61K}$ RXRα$^{L2/L2}$ (RXR+) mice represent a model with increased latency to develop invasive melanoma while Tyr NRAS$^{Q61K}$ RXRα$^{ep-/-}$ (RXR−) bigenic mice, selectively lacking RXRα in the epidermis alongside with the activating NRAS mutation in the melanocytes, represent a metastatic melanoma model where melanoma cells readily migrate and invade the lymphatics. Analysis of melanocyte covered pigmented area comparing RXR+ and RXR− for the three-drug nanoparticles with same charge distribution indicated that no statistically significant difference was demonstrated (FIGS. 14 and 15), thereby indicating that the nanoparticles retained efficacy across the two different melanoma models.

In summary, a three-drug (DTX, EVR, and LY) nanoparticle was developed and characterized that acted synergistically in vivo in two different melanoma mouse models. The results indicated that the effect of the three-drug neutral nanoparticles was proximal to the site of injection, while the three-drug partially charged nanoparticles tracked further into the lymphatic system reaching more distal LNs. In contrast, the three-drug fully charged nanoparticles had minimal effects on the proximal or distal LN. The three-drug combination neutral and partially charged nanoparticles were highly effective in treating melanoma in both models, and provide the basis for a novel therapeutic option treating metastatic melanoma that is targeted to the site of action i.e. the lymphatic system.

III. Dosages

The present disclosure provides pharmaceutical compositions that include a therapeutically effective amount of one or more disclosed drug-loaded nanoparticles (such as 1, 2, 3, 4 or 5 disclosed compounds) in admixture with at least one pharmaceutically acceptable material, such as an excipient. Disclosed pharmaceutical compositions include a detectable amount of the drug-loaded nanoparticles, such as greater than 0% to less than 100%, such as from 5% to 99%, or from about 50% to about 99%, or from 25% to about 99% by weight of the drug-loaded nanoparticles of the present disclosure.

The particular mode of administration and the dosage regimen will be selected by the attending clinician, taking into account the particulars of the case (e.g. the subject, the disease, the disease state involved, and the particular treatment). Treatment can involve daily or multi-daily or less than daily (such as weekly or monthly etc.) doses over a period of a few days to months, or even years. For example, a therapeutically effective amount of one or more drug-loaded nanoparticles disclosed herein can be administered in a single dose, twice daily, weekly, or in several doses, for example daily such as two, three or four times daily, or during a course of treatment.

The pharmaceutical compositions that include one or more drug-loaded nanoparticles disclosed herein can be formulated in unit dosage form, suitable for individual administration of precise dosages. In some embodiments, a therapeutically effective amount of the drug-loaded nanoparticles is an amount sufficient to provide a therapeutically effective amount of the one or more drugs encapsulated within the nanoparticles. The therapeutically effective amount of drug-loaded nanoparticles may be sufficient to provide from greater than zero to 100 mg/kg or more of the one or more drugs, such as from 5 mg/kg to 50 mg/kg, from 10 to 30 mg/kg, or about 20 mg/kg of the one or more drug. In one non-limiting example, a unit dosage of the nanoparticles contains from about 1 mg to about 50 g of one or more drug-loaded nanoparticles disclosed herein, such as about 10 mg to about 10 g, about 100 mg to about 10 g, about 100 mg to about 7 g, about 200 mg to about 10 g, or about 200 mg to about 5 g. In other examples, a therapeutically effective amount of one or more drug-loaded nanoparticles disclosed herein is from about 0.01 mg/kg to about 500 mg/kg, for example, about 0.5 mg/kg to about 500 mg/kg, about 1 mg/kg to about 100 mg/kg, or about 1 mg/kg to about 50 mg/kg. In other examples, a therapeutically effective amount of one or more drug-loaded nanoparticles disclosed herein is from about 1 mg/kg to about 20 mg/kg, such as about 2 mg/kg to about 5 mg/kg. In some embodiments, about 3 mg/kg, 10 mg/kg, or 20 mg/kg can be used.

IV. Examples

EXAMPLE 1

Nanoparticles Loaded with a Combination of DTX, EVR and LY Materials

The polymers, methoxy poly (ethylene glycol)-block-poly (ε-caprolactone) (mPEG$_{5000}$-b-PCL$_{10000}$) [Mn=15000; PDI=1.17] and carboxy poly (ethylene glycol)-block-poly (ε-caprolactone) COOH-PEG$_{5000}$-b-PCL$_{10300}$ [Mn=15300; PDI=1.39] were purchased from Advanced Polymer Materials Inc. (Montreal, CAN). DTX, EVR, and LY were purchased from LC laboratories (Woburn, Mass.). Slide-A-Lyzer™ Dialysis Cassettes, 20K MWCO were obtained from Thermo Scientific Inc. (Fairlawn, N.J.). A375 human melanoma epithelial cells were obtained from American Type Culture Collection (Manassas, Va.). Two metastatic melanoma mice models, Tyr NRAS$^{Q61K}$ RXRα$^{L2/L2}$ and Tyr NRAS$^{Q61K}$ RXRα$^{ep-/-}$, were generated according to previous work. CellTiter-Blue® Cell viability Assay was obtained from Promega Inc. (Madison, Wis.). Fontana-Masson stain kit was purchased from American Mastertech Scientific, Inc. (Lodi, Calif.). All reagents and supplies were purchased from VWR International, LLC (Radnor, Pa.) or Fischer Scientific Inc. (Fairlawn, N.J.).

Methods

Preparation and Characterization of Three-Drug Loaded Nanoparticles

DTX, EVR and LY three-drug nanoparticles were prepared using a solvent evaporation method. Briefly, 40 mg of the PEG-PCL polymers at various concentrations were dissolved in 2 mL of acetone. For neutral nanoparticles only mPEG-PCL (neutral nanoparticles) was used, while for partially charged nanoparticles, a mixture of mPEG:COOHPEG (60:40) (partially charged nanoparticles) with PCL was used. For the fully charged nanoparticles, 100% COOHPEG-PCL (fully charged nanoparticles) was used. Stock solutions of DTX, EVR, and LY in acetone were prepared and required concentrations were added to the polymer solution to achieve a final concentration of 2 mg/mL of each drug. That is there were 2 mg of each drug per mL of the nanoparticle solution. The drug polymer solution was transferred into a 10 mL round bottom flask and normal saline, 2 mL, was added, followed by removal of the organic solvent using a rotary evaporator. The evaporation cycle was divided into three segments, with the first segment lasting 7 minutes at 420 mbar, the second for 7 minutes at 320 mbar, and the final segment of 6 minutes at 200 mbar. The temp of the water bath was maintained at 45° C. with a rotation of 100 rpm for the round bottom flask. The final volume was adjusted to 2 mL with saline. The nanoparticles were collected in a centrifuge tube and spun at 5,000 rpm for 3 minutes and filtered/sterilized using a 0.2 µm nylon filter prior to use.

Nanoparticles were characterized for size, surface charge distribution, and drug loading. Particle size was characterized by Dynamic Light Scattering (DLS) using a Malvern Nano ZS (Malvern Instruments Inc., U.K.). All measurements were performed in triplicate and data is presented as the mean z-average diameter±SD (nm) and polydispersity index (PDI±SD). Statistical analysis (one way ANOVA) was performed using Graph Pad Prism software to determine statistical significance between the sizes of the empty, partially charged, and fully charged nanoparticles. The surface charge was measured using the same instrument and the data of three replicates is presented as mean zeta potential ($\zeta$)±SD (mV). The drug loading was determined by reverse-phase high performance liquid chromatography (RP-HPLC) using a Shimadzu HPLC system consisting of LC-20 AT pump and SPD M20 a diode array detector. The analysis was performed using Zorbax C8 Column (4.6×75 mm, 3.5 µm) in isocratic mode with acetonitrile/water (62/38) containing 0.1% phosphoric acid and 1% methanol at a flow rate of 1 mL/min and an injection volume of 10 µL. Column temperature was maintained at 40° C. The DTX, EVR, and LY peaks were monitored at 227 nm, 279 nm, and 303 nm respectively at retention times of 1.7, 5.7, and 2.0 minutes respectively. All measurements were performed in triplicate and loading data are presented as mean drug loading (mg/mL)±SD.

In Vitro Drug Release from the Nanoparticles

The three-drug nanoparticles were prepared as described above. The release profiles of DTX, EVR, and LY from neutral, partially charged, and fully charged nanoparticles were evaluated over 48 hours in 10 mM phosphate buffer pH 7.4 at 37° C. under sink conditions by dialysis. Briefly, in three separate dialysis cassettes, for each type of nanoparticle, 2.0 mL of the sample was loaded. A MWCO of 20,000 Da was chosen to enable the unhindered diffusion of free drugs along with the unassociated polymer molecules out of the cassette. The cassettes were placed in 2.5 L of phosphate buffer and the temperature was maintained at 37° C. for the duration of the experiment. Sink conditions were ensured by changing the buffer every 3 hours. Samples of 20 µL were withdrawn at 0, 0.5, 1, 2, 3, 6, 12, 24, and 48 hours and were replaced with an equal volume of fresh buffer. Samples were diluted 50 fold in the mobile phase and analyzed by RP-HPLC for drug content. The data is presented as mean % drug release±SD. Data were curve fitted using a two phase exponential association equation in Graph Pad Prism 5 software. The time required to release 50% of the drug ($t_{1/2}$) in two phases, fast and slow, and the goodness of fit ($r^2$) values of three replicates are presented. Statistical Analysis using one-way ANOVA with Tukey's post-test was performed on the release profiles for each drug across the different NP to assess for differences in rates of drug release. Statistical analysis was performed using GraphPad Prism 5 software.

In Vitro Cell Viability Assay and Combination Index (CI) Analysis

A375 human malignant epithelial melanoma cells were seeded at a density of 5,000 cells/well in 96 well plates and allowed to attach for 12 hours at 37° C. Post-attachment, cells were treated with individual drugs (DTX, EVR, or LY) or two drugs (DTX:EVR, DTX:LY, or EVR:LY at 1:1 molar ratios) or three drugs (DTX:EVR:LY 1:1:1 or 1:1:2 molar ratios) dissolved in DMSO. The three-drug neutral, partially charged, and fully charged nanoparticles were also assessed at 1:1:2 molar ratio. The concentration range for all three drugs was between 0.01-10,000 nM. The final concentration of DMSO in the wells was 1%. Cell viability was determined after 48 hours by treatment with 20 µL of CellTiter-Blue® reagent followed by one hour of incubation at 37° C. and fluorescence intensity ($560_{EX}/590_{EM}$) was measured. All measurements were performed in triplicate. The drug concentration at 50% growth inhibition ($IC_{50}$) was determined by the linearized median-effect plot using Compusyn software (Version 1.0, ComboSyn Inc., U.S.) based on Chou and Talalay median-effect principle. The combination effect of DTX:EVR, DTX:LY, EVR:LY, and DTX:EVR:LY in DMSO in A375 cells was also evaluated using Compusyn software. Combination Index (CI) values of <1, 1, and >1 are indicative of synergy, additivity, and antagonism respectively. The software also generates CI values at various fractions of cells affected (Fa). The Fa value is proportional to the dose and therefore Fa vs CI plots can provide the interactive effects of the combinations over the various doses tested. The data, in triplicate, is presented as Fa vs CI plots to correlate the effect of the combinations at different treatment concentrations.

Figure 16:
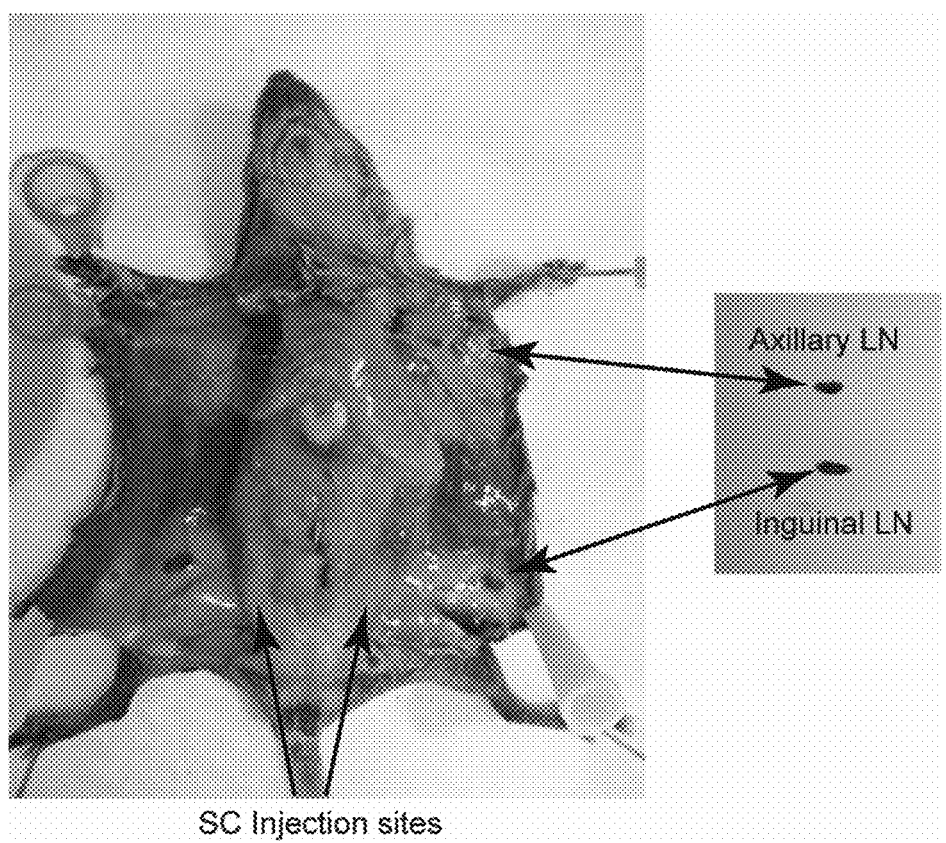
FIG. 16 is a photograph of a mouse showing the phenotypic appearance of Tyr NRAS$^{Q61K}$ RXRα$^{L2/L2}$ (RXR+) or Tyr NRAS$^{Q61K}$ RXRα$^{ep-/-}$ (RXR−) with injection site and lymph nodes of interest (Inguinal and Axillary).

In Vivo Assessment of Safety and Efficacy in Tyr NRAS$^{Q61K}$ RXR$\alpha^{L2/L2}$ and Tyr NRAS$^{Q61K}$ RXR$^{ep-/-}$ Metastatic Melanoma Mouse Models Tyr NRAS$^{Q61K}$ RXR$\alpha^{L2/L2}$ (RXR+) and Tyr NRAS$^{Q61K}$ RXR$\alpha^{ep-/-}$ (RXR-) metastatic melanoma mouse models with the two major mutations (NRAS$^{Q61k}$ and RXR$\alpha$) found in human melanoma were used for the in vivo studies. The generation of Tyr NRAS$^{Q61K}$ mice has been previously described. See Coleman, D. J.; et al., "Retinoid-X-receptors (alpha/beta) in melanocytes modulate innate immune responses and differentially regulate cell survival following UV irradiation." *PLoS Genet* 2014, 10, e1004321, which is incorporated herein by reference in its entirity. The mice were housed in ventilated cages with free access to food and water and were maintained at controlled temperature and humidity conditions for the duration of the experiment. Animals that were 8-12 weeks old were sorted into 2 major categories (RXR+ or RXR−). In each category, mice were subdivided into 7 groups with 4 animals per group. The groups included control untreated mice, control empty nanoparticles of each charge distribution, and treatment drug loaded nanoparticles of each charge distribution for a total of 28 animals per model (n=56 for both models). Each group, except the untreated group, was treated with empty or three-drug loaded neutral, partially charged, or fully charged nanoparticles. Animals were injected SC (every week×3 cycles) proximal to the inguinal (FIG. 16) LN with 150 μL/side (total volume 300 μL) of the empty or three-drug loaded nanoparticles. Each animal received a dose of 20 mg/kg of each drug with a total dose of 60 mg/kg for all three drugs in the treatment groups and the dose of the polymer was approximately 20 mg/kg for all injected nanoparticles.

During the study (21 days), mice were monitored for signs of acute toxicity such as noticeable changes in general appearance, loss in median body weight ≥15%, or death. On day 21, 7 days post last injection, mice were euthanized and blood samples were collected, centrifuged at 3,000×g for 7 minutes and the plasma samples were submitted for complete blood panel chemistry analysis. The analysis was performed at Oregon State University Veterinary Diagnostic Laboratory. The concentrations of blood urea nitrogen (BUN), creatinine, alanine transaminase (ALT), and creatinine kinase (CK) values were assessed. BUN and creatinine are surrogate markers for kidney toxicity while ALT and CK are surrogate markers for heart and liver toxicity. The quantified values between the treatment and the control groups for both models were compared by one-way ANOVA with Tukey's multiple comparison post-test at a p-value of 0.05 using Graph Pad prism version 5.00 for Windows to assess organ toxicity. Data are presented as mean parameter value±S.D of four replicates.

Immediately post- euthanasia and blood collection the inguinal and axillary LN (FIG. 16) were collected and stored at −80° C. to evaluate the efficacy in terms of reduction in melanocytes in response to the treatment. Briefly, LN were fixed in 4% paraformaldehyde and were embedded in paraffin blocks. For histological studies, 5 μm-thick paraffin sections from mouse LN were rehydrated and Fontana-Masson (FM) staining was performed according to manufacturer's instructions. FM selectively stains black for any melanin containing cells (melanocytes) and stains pink for the nuclei. FM staining of skin-draining LNs is used as a general label for melanin pigment, which represent pigment-producing (melanocytic) cells, the nuclei are stained pink using a secondary Nuclear Red dye for contrast. All microscopic studies were conducted using Leica DME light microscope and analyzed using Leica Application Suite software, version 3.3.1. Images were taken using 20X objective throughout the study. Post staining, quantifications of melanin pigmented area were performed using Adobe Photoshop CS5 software. The pictures of LN were analyzed independently in a double-blind manner by two investigators, and significance was determined using a Student's two-tailed unpaired t-test as calculated by Graph Pad Prism software. Data are presented as mean # of melanocytes/pigmented area±SD in inguinal or axillary LN for four replicates.

EXAMPLE 2

Nanoparticles Loaded with a Combination of TRA and DAB

Preparation and Characterization of TRA:DAB Loaded Nanoparticles

Figure 17A:
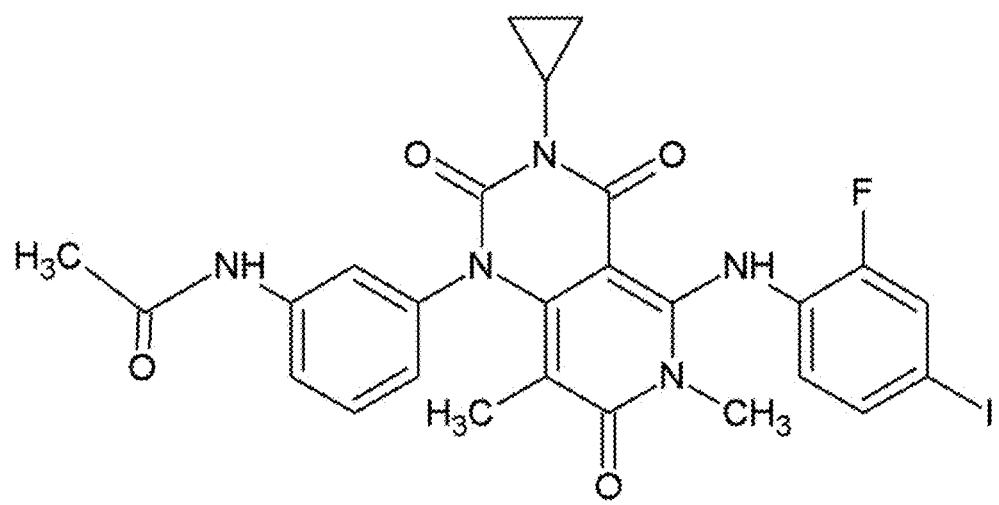
FIG. 17A shows the structure of trametinib (TRA).
Figure 17B:
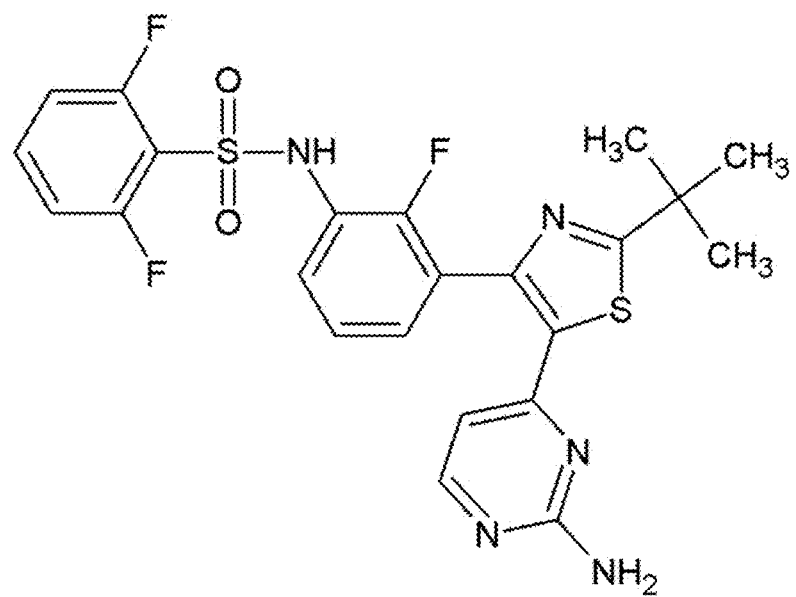
FIG. 17B shows the structure of dabrafenib (DAB).
Figure 18:
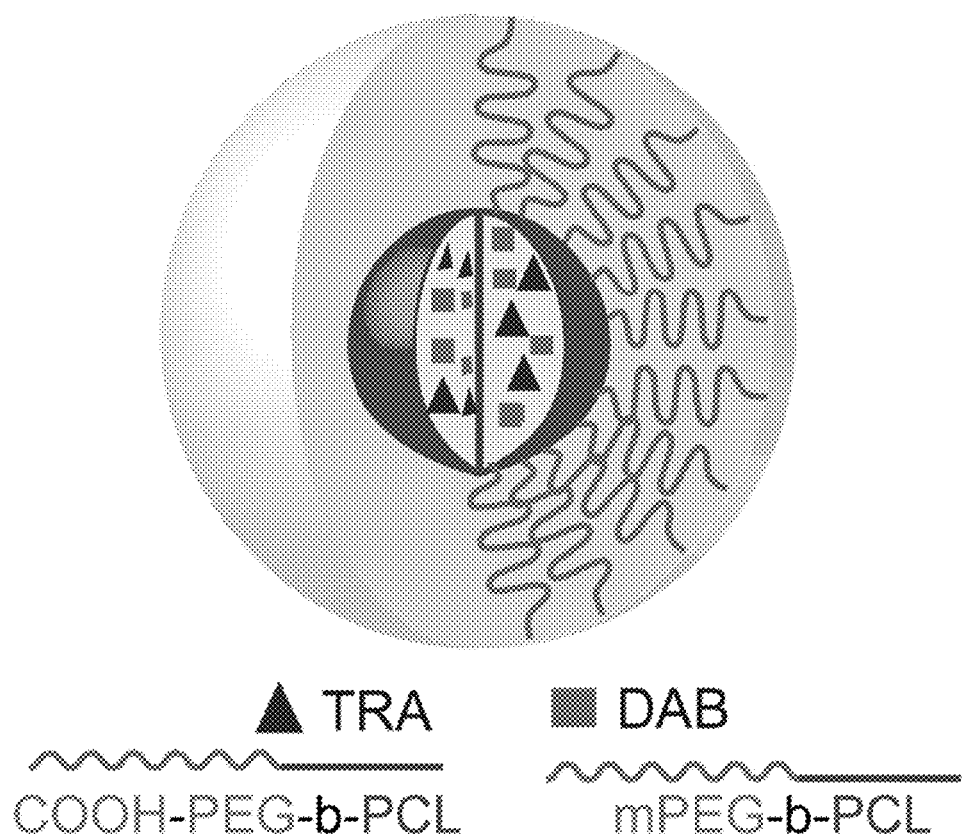
FIG. 18 is a schematic diagram illustrating the two drugs from FIGS. 17A and 17B loaded into a nanoparticle.

Structures for the TRA and DAB are depicted in FIGS. 17A and 17B, and a representation of a two-drug loaded nanoparticle comprising TRA and DAB is depicted in FIG. 18.

Figure 19:
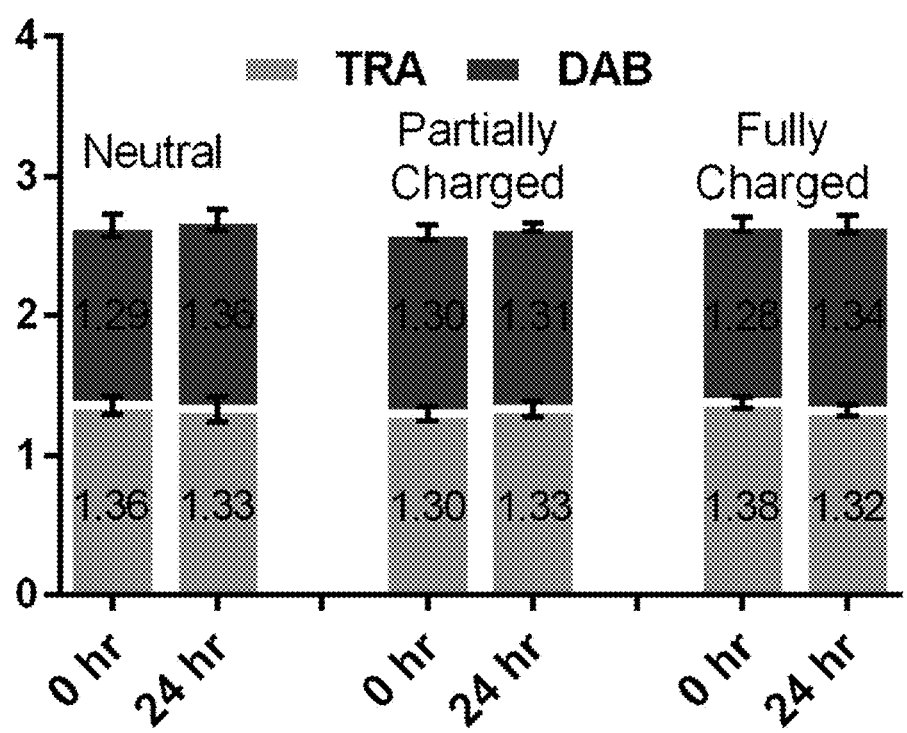
FIG. 19 is a graph of concentration versus time illustrating the initial loading and drug retention at 24 hours for TRA and DAB in two-drug neutral, partially charged, and fully charged nanoparticles (Mean±S.D, n=3).

The neutral, partially charged and fully charged drug-loaded nanoparticles were prepared by the method described in Example 1. Nanoparticles were able to solubilize approximately 1.3 mg of each drug per mL of nanoparticle solution and retain each of the drugs at the initial concentrations (within 1-2%) for 24 hours (FIG. 19). The zeta potential and particle size of the nanoparticles were the same as those listed in Table 1. The final molar ratios for the three drugs in the nanoparticles were about 1:1 of TRA:DAB. The intrinsic aqueous solubilities of TRA, and DAB were 6 μg/mL and 1 μg/mL respectively. Thus, incorporation of these drugs into the nanoparticles increased the solubility of TRA and DAB by 221 and 1000 fold respectively, thereby achieving therapeutically relevant dosing concentrations for in vivo assessment.

In Vitro Cell Viability Assay

Figure 20:
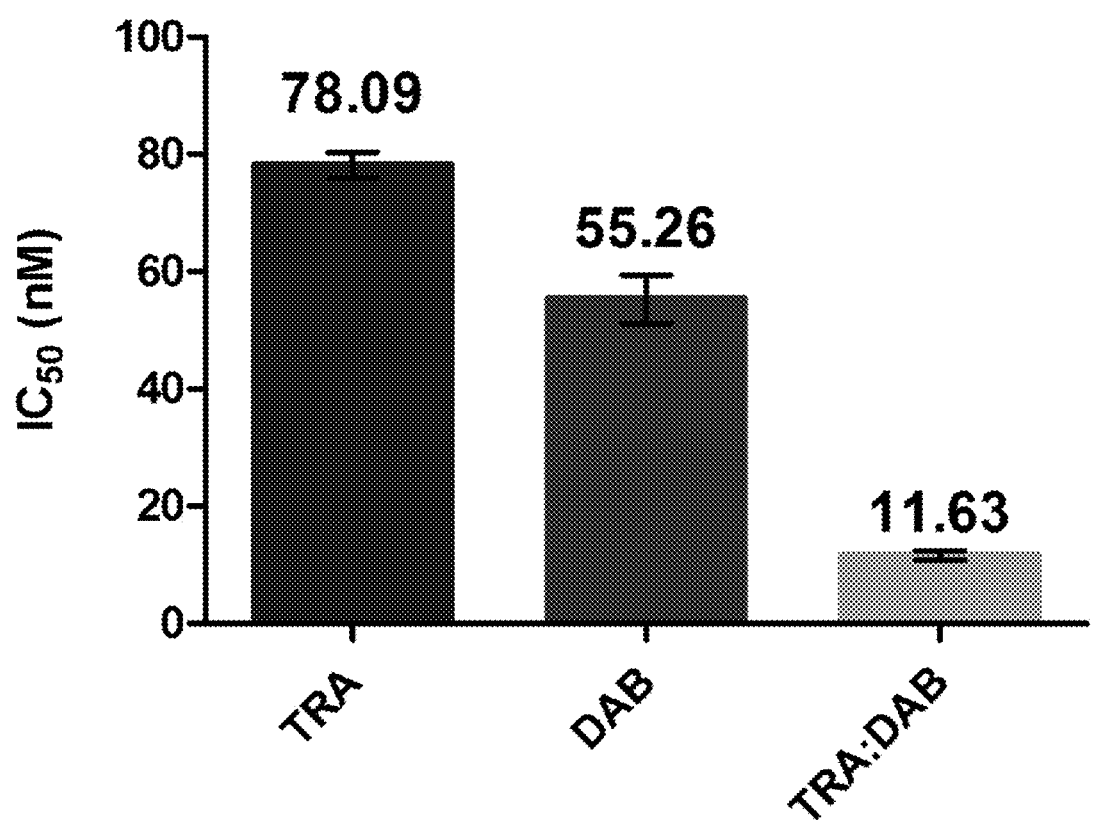
FIG. 20 is a graph of $IC_{50}$ versus drug regime illustrating the mean $IC_{50}$ values for TRA, DAB, and a two-drug combination in DMSO in A375 metastatic melanoma cells.

The anti-proliferative effects ($IC_{50}$ values) of TRA and DAB in DMSO individually and in two-drug combinations evaluated in A375 human melanoma cells are presented in FIG. 20. The two-drug combinations (1:1 molar ratio) in DMSO exhibited strong inhibition of A375 cell proliferation over a wide range of tested doses. As the prepared nanoparticles were at 1:1 molar ratio of TRA:DAB, the 1:1 ratio of these drugs in DMSO was also evaluated for anti-proliferative effects in the cell line. Based on the data (FIG. 20) the two-drug combinations were more potent than the individual drug treatments, with potency at 11.63 nM concentration, illustrating at least an additive effect.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A composition comprising a drug and a charged nanoparticle comprising a combination of carboxy poly (ethylene glycol)-block-poly (ε-caprolactone) and a polyethyleneglycol-block-poly (ε-caprolactone) (PEG-PCL), the nanoparticle encapsulating the drug and having a size and a zeta potential effective to cause uptake of the composition into at least a first and a second lymph node of a subject to which the composition is administered, the first lymph node being proximal to a site of administration of the composition and the second lymph node being distal to the site of administration, the nanoparticle having a zeta potential of from −1 mV to −20 mV.

2. The composition of claim 1, wherein the nanoparticle comprises a combination of methoxy poly (ethylene glycol)-block-poly (ε-caprolactone) and carboxy poly (ethylene glycol)-block-poly (ε-caprolactone).

3. The composition of claim 1, wherein drug is docetaxel, everolimus, LY294002, paclitaxel, rapamycin, irinotecan, ixabepilone, vinblastine, vinorelbine, estramustine, vemurafenib, trametinib, dabrafenib or a combination thereof.

4. The composition of claim 1, wherein the composition comprises docetaxel, everolimus and LY294002.

5. The composition of claim 1, wherein the composition comprises trametinib and dabrafenib.

6. The composition of claim 1, wherein the nanoparticle has a zeta potential of from −10 mV to −20 mV.

7. The composition of claim 1, wherein the nanoparticle has a size of from 20 nm to 80 nm.

8. The composition of claim 1, wherein each drug has a drug concentration of about 0.5-2 mg of drug per mL of nanoparticle solution.

9. The composition of claim 1, wherein the drug comprises docetaxel, everolimus and LY294002, the zeta potential is from −15 mV to −20 mV, and the nanoparticle has a size of from 40 nm to 50 nm.

10. The composition of claim 1, comprising trametinib and dabrafenib, encapsulated in a polyethyleneglycol-block-poly (ε-caprolactone)/carboxy poly (ethylene glycol)-block-poly (ε-caprolactone) nanoparticle having a zeta potential of from −15 mV to −20 mV and a size of from 40 nm to 50 nm.

11. A pharmaceutical composition comprising the composition of claim 1, and a pharmaceutically acceptable carrier or excipient.

12. A method of treating a cancer in a subject, the method comprising administering to the subject a therapeutically effective amount of a composition of claim 1, wherein the cancer is cutaneous melanoma, inflammatory breast carcinoma, non-small cell lung cancer, muscle-invasive transitional cell carcinoma of the bladder, head and neck cancer, or a combination thereof.

13. The method of claim 12, wherein administering to the subject comprises administering the composition subcutaneously or intramuscularly.

14. The method of claim 12, wherein the therapeutic amount is an amount sufficient to decrease the number of melanocytes in at least one lymph node of the subject.

15. The method of claim 14, wherein the therapeutic amount is an amount sufficient to decrease the number of melanocytes in lymph nodes both proximal and distal to a site of administration.

16. The method of claim 14, wherein the amount of the composition is sufficient to be disseminated to lymph nodes throughout the lymphatic system.

17. A composition, comprising a combination of drugs comprising docetaxel, everolimus and LY294002, and a nanoparticle encapsulating the combination of drugs, the nanoparticle comprising methoxy poly (ethylene glycol)-block-poly (ε-caprolactone) and carboxy poly (ethylene glycol)-block-poly (ε-caprolactone).

* * * * *